United States Patent
Tsunoda et al.

(10) Patent No.: US 8,367,799 B2
(45) Date of Patent: Feb. 5, 2013

(54) EM8 PEPTIDES AND VACCINES COMPRISING THE SAME

(75) Inventors: Takuya Tsunoda, Kanagawa (JP); Ryuji Osawa, Kanagawa (JP)

(73) Assignee: OncoTherapy Science, Inc., Kanagawa (JP)

( * ) Notice: Subject to any disclaimer, the term of this patent is extended or adjusted under 35 U.S.C. 154(b) by 436 days.

(21) Appl. No.: 12/595,197

(22) PCT Filed: Apr. 10, 2008

(86) PCT No.: PCT/JP2008/000932
§ 371 (c)(1),
(2), (4) Date: Mar. 22, 2010

(87) PCT Pub. No.: WO2008/126413
PCT Pub. Date: Oct. 23, 2008

(65) Prior Publication Data
US 2012/0093843 A1 Apr. 19, 2012

Related U.S. Application Data

(60) Provisional application No. 60/911,194, filed on Apr. 11, 2007.

(51) Int. Cl.
*C07K 5/00* (2006.01)
(52) U.S. Cl. ....... 530/326; 530/327; 530/328; 514/21.5; 514/21.6
(58) Field of Classification Search .................. None
See application file for complete search history.

(56) References Cited

U.S. PATENT DOCUMENTS

| | | | |
|---|---|---|---|
| 6,426,205 B1 * | 7/2002 | Tyers et al. | 435/194 |
| 6,465,717 B1 * | 10/2002 | Famodu et al. | 800/278 |
| 6,936,707 B2 * | 8/2005 | Okuda et al. | 536/23.7 |
| 7,074,913 B2 * | 7/2006 | Young et al. | 536/23.7 |
| 7,112,717 B2 * | 9/2006 | Valentin et al. | 800/278 |
| 7,160,994 B2 * | 1/2007 | Choi | 536/23.1 |
| 7,358,351 B2 * | 4/2008 | St. Croix et al. | 536/23.1 |
| 2003/0092616 A1 * | 5/2003 | Matsuda et al. | 514/12 |

FOREIGN PATENT DOCUMENTS

| | | |
|---|---|---|
| EP | 1548032 A1 | 6/2005 |
| EP | 1 710 299 A2 | 10/2006 |
| JP | 2006-52216 A | 2/2006 |
| WO | WO 2004/024766 A1 | 3/2004 |
| WO | 2005/048943 * | 6/2005 |
| WO | WO 2005/048943 A2 | 6/2005 |
| WO | WO 2008/000734 A1 | 1/2008 |

OTHER PUBLICATIONS

Calin-Laurens, V., et al., "Can one predict antigenic peptides for MHC class I-restricted cytotoxic T lymphocytes useful for vaccination?," *Vaccine*, vol. 11(9), pp. 974-978 (1993).
Stuber, G., et al., "Assessment of major histocompatibility complex class I interaction with Epstein-Barr virus and human immunodeficiency virus peptides by elevation of membrane H-2 and HLA in peptide loading-deficient cells," *Eur. J. Immunol.*, vol. 22(10), pp. 2697-2703 (Oct. 1992).
Komori, H., et al., "Identification of HLA-A2- or HLA-A24-Restricted CTL Epitopes Possibly Useful for Glypican-3-Specific Immunotherapy of Hepatocellular Carcinoma," *Clinical Cancer Research*, vol. 12(9), pp. 2689-2697 (May 1, 2006).
Kondo, A., et al., "Prominent roles of secondary anchor residues in peptide binding to HLA-A24 human class I molecules," *The Journal of Immunology*, vol. 155(9), pp. 4307-4312 (Nov. 1, 1995).
Kubo, RT., et al., "Definition of specific peptide motifs for four major HLA-A alleles," *The Journal of Immunology*, vol. 152(8), pp. 3913-3924 (Apr. 15, 1994).
Tokunaga, et al., "Sequence-based association analysis of HLA class I and II alleles in Japanese supports conservation of common haplotypes," *Immunogenetics*, vol. 46(3), pp. 199-205 (1997).
Zaremba, S., et al., "Identification of an Enhancer Agonist Cytotoxic T Lymphocyte Peptide from Human Carcinoembryonic Antigen," *Cancer Research*, vol. 57(20), pp. 4570-4577 (Oct. 15, 1997).
Mignot, G., et al., "Prospects for exosomes in immunotherapy of cancer," *J. Cell Mol. Med.*, vol. 10(2), pp. 376-388 (Apr.-Jun. 2006).
Dionne, et al., "Functional characterization of CTL against gp100 altered peptide ligands," *Cancer Immunol Immunother.*, vol. 52(4), pp. 199-206 (Apr. 2003, Epub Feb. 18, 2003).
Dionne, et al., "Her-2/neu altered peptide ligand-induced CTL responses: implications for peptides with increased HLA affinity and T-cell-receptor interaction," *Cancer Immunol Immunother.*, vol. 53(4), pp. 307-314 (Apr. 2004, Epub Nov. 5, 2003).
Falk, et al., "Allele-specific motifs revealed by sequencing of self-peptides eluted from MHC molecules," *Nature*, vol. 351(6324), pp. 290-296 (May 23, 1991).
Hoffman, "The Ability of Variant Peptides to Reverse the Nonresponsiveness of T Lymphocytes to the Wild-Type Sequence $p53_{264-272}$ Epitope," *J Immunol.*, vol. 168(3), pp. 1338-1347 (Feb. 1, 2002).
Rammensee, et al., "MHC ligands and peptide motifs: first listing," *Immunogenetics*, vol. 41(4), pp. 178-228 (1995).
St. Croix, et al., GenBank: AAK52094.1, (http://www.ncbi.nlm.nih.gov/protein/AAK52094.1), 2 pages, retrieved Feb. 2, 2012 (May 9, 2001).
Xiang, et al., "Induction of specific immunity against tumor endothelial cells by dendritic cells in vitro," Xi Bao Yu Fen Zi Mian Yi Xue Za Zhi, vol. 21(4), pp. 495-498 (Jul. 2005).
Roitt, et al., Immunology, M: Mir, pp. 159, 160-162 (2000).
Strausberg, et al., UNIPROT Accession No. Q96EC6, 2 pages, retrieved from http://www.ncbi.nlm.nih.gov/protein/Q96EC6 (sequence updated Dec. 1, 2001, downloaded Sep. 6, 2012).

(Continued)

*Primary Examiner* — Sheela J Huff
(74) *Attorney, Agent, or Firm* — Kilpatrick Townsend & Stockton LLP

(57) ABSTRACT

According to the present invention, peptides comprising the amino acid sequence of SEQ ID NO: 3, 4, 9, 23, 25, 30, 60, 63 or 68 were demonstrated to have cytotoxic T lymphocyte (CTL) inducibility. Therefore, the present invention provides a peptide having the amino acid sequence selected from the group of SEQ ID NOs: 3, 4, 9, 23, 25, 30, 60, 63 and 68. The peptide can include one, two, or several amino acid substitutions or addition so long as its CTL inducibility is retained. Furthermore, the present invention provides pharmaceutical agents for treating and/or prophylaxis of tumors, and/or prevention of postoperative recurrence thereof, which comprises any of these peptides. The pharmaceutical agents of this invention include vaccines.

9 Claims, 5 Drawing Sheets

OTHER PUBLICATIONS

Lee, et al., "Increased Vaccine-Specific T Cell Frequency After Peptide-Based Vaccination Correlates with Increased Susceptibility to in Vitro Stimulation But Does Not Lead to Tumor Regression," *J Immunol.*, vol. 163(11), pp. 6292-6300 (Dec. 1, 1999).

Roitt, et al., Immunology, translation from English, M. Mir 2000: 10-13.

Roitt, et al., Immunology, translation from English, M. Mir 2000: 194-199.

* cited by examiner a b

TEM8 PEPTIDES AND VACCINES COMPRISING THE SAME

CROSS-REFERENCE TO RELATED APPLICATIONS

The present application is a U.S. National Stage Application of PCT/JP2008/000932, filed Apr. 10, 2008, which claims the benefit of U.S. Provisional Application No. 60/911,194, filed on Apr. 11, 2007, the entire disclosures of which are hereby incorporated herein by reference in their entirety for all purposes.

TECHNICAL FIELD

Field of the Invention

The present invention relates to the field of biological science, more specifically to the field of cancer therapy. In particular, the present invention relates to TEM8 peptides that are extremely effective as cancer vaccines, and drugs for treating and prevention of tumors.

BACKGROUND ART

It has been demonstrated that CD8 positive cytotoxic T lymphocytes (CTLs) recognize epitope peptides derived from tumor-associated antigens (TAAs) on major histocompatibility complex (MHC) class I molecule, and then kill the tumor cells. Since the discovery of the melanoma antigen (MAGE) family as the first example of TAAs, many other TAAs have been discovered through immunological approaches (Boon T, Int J Cancer 1993 May 8, 54(2): 177-80; Boon T & van der Bruggen P, J Exp Med 1996 Mar. 1, 183(3): 725-9), and some of the TAAs are now in the process of clinical development as immunotherapeutic targets.

Identification of new TAAs, which induce potent and specific anti-tumor immune responses, warrants further development of clinical application of peptide vaccination strategies in various types of cancer (Harris C C, J Natl Cancer Inst 1996 Oct. 16, 88(20): 1442-55; Butterfield L H et al., Cancer Res 1999 Jul. 1, 59(13): 3134-42; Vissers J L et al., Cancer Res 1999 Nov. 1, 59(21): 5554-9; van der Burg S H et al., J Immunol 1996 May 1, 156(9): 3308-14; Tanaka F et al., Cancer Res 1997 Oct. 15, 57(20): 4465-8; Fujie T et al., Int J Cancer 1999 Jan. 18, 80(2): 169-72; Kikuchi M et al., Int J Cancer 1999 May 5, 81(3): 459-66; Oiso M et al., Int J Cancer 1999 May 5, 81(3): 387-94). Until now, several clinical trials using these tumor-associated antigen derived peptides have been reported. Unfortunately, only a low objective response rate could be observed in these cancer vaccine trials so far (Belli F et al., J Clin Oncol 2002 Oct. 15, 20(20): 4169-80; Coulie P G et al., Immunol Rev 2002 October, 188: 33-42; Rosenberg S A et al., Nat Med 2004 September, 10(9): 909-15).

One possible reason for this relative lack of efficacy could be the loss or down-regulated expression of human leukocyte antigen (HLA) class I molecules on tumor cells, which frequently occurs in solid tumors and severely impairs T cell-mediated anti-tumor responses (Cormier J N et al., Int J Cancer 1998 Feb. 9, 75(4): 517-24; Hicklin D J et al., Mol Med Today 1999 April, 5(4): 178-86; Paschen A et al., Int J Cancer 2003 Mar. 1, 103(6): 759-67). Even if potent cytotoxic T lymphocytes (CTLs) are induced by cancer vaccine targeting tumor associated antigens, the CTLs fail to recognize the target cells when they do not express a sufficient amount of HLA class I molecules.

Tumor angiogenesis is critically involved in the progression of tumors. It has been already demonstrated that an effective vaccine against tumor angiogenesis could be developed according to an endothelial cell-based approach, targeting vascular endothelial growth factor receptors (VEGFRs) 1 and 2, as HLA class I molecules are not down-regulated on endothelial cells (Wada S et al., Cancer Res 2005 Jun. 1, 65(11): 4939-46; Ishizaki H et al., Clin Cancer Res 2006 Oct. 1, 12(19): 5841-9). Moreover, since these therapeutic targets are tumor-independent, the depletion of vascular endothelial cells in the tumor microenvironment could be effective against a variety of malignancies. Furthermore, tumor endothelial cells are readily accessed by lymphocytes in the bloodstream, and CTLs can directly damage endothelial cells without the penetration of any other tissue type. In addition, the lysis of even a small number of endothelial cells within the tumor vasculature may result in the destruction of vessel integrity, thus leading to the inhibition of numerous tumor cells (Folkman J, Nat Med 1995 January, 1(1): 27-31). Therefore, tumor endothelial cells are a good target for cancer immunotherapy. In order to suppress tumor angiogenesis with a specific and efficient CTL response, an appropriate target needs to be selected among molecules that are related to angiogenesis.

Tumor endothelial markers (TEMs) including TEM8, have been found to be specifically elevated in tumor-associated endothelium compared with normal tissue (St Croix B et al., Science 2000 Aug. 18, 289(5482): 1197-202). The TEM8 transcript was expressed in lung and brain tumor and liver metastasis. Therapy targeting TEM8 is applicable to a wide range of tumor types. For example, WO 2005/048943 proposes the use of vaccines comprising a vector encoding the extracellular domain of TEM8 with a vaccine encoding tumor-associated antigen. However, this document fails to provide any evidence that the introduction of the TEM8-expressing vector resulted in the induction of CTLs against tumor-associated endothelium, nor does it provide any information on the position of epitopes within the TEM8 protein.

DISCLOSURE OF INVENTION

Summary of the Invention

It is important to improve the clinical efficacy for cancer treatment targeting tumor microenvironment, especially for those targeting tumor angiogenesis. The present invention focuses on tumor blood vessels as the target for anti-tumor immunotherapy. In particular, the invention targets the tumor endothelial marker 8 (TEM8) (GenBank Accession No. NP_115584 (SEQ ID NO: 76) encoded by the gene of GenBank Accession No. NM_032208 (SEQ ID NO: 75)), since TEM8 has been thought to be expressed in vessels of a wide range of tumor types. The present invention provides TEM8 gene products containing epitope peptides that elicit CTLs specific to the corresponding molecules. Peripheral blood mononuclear cells (PBMCs) obtained from a healthy donor were stimulated using HLA-A*2402 or HLA-A*0201 binding candidate peptides derived from TEM8. The present invention further provides established CTLs that specifically recognize HLA-A24 or HLA-A02 positive target cells pulsed with the respective candidate peptides, and HLA-A24 or HLA-A02 restricted epitope peptides that can induce potent and specific immune responses against TEM8 expressed on tumor blood vessels. These results demonstrate that TEM8 is strongly immunogenic and the epitopes thereof are effective targets for tumor immunotherapy.

Accordingly, the present invention provides an isolated nonapeptide or decapeptide having cytotoxic T cell inducibility, wherein said nonapeptide or decapeptide comprises an amino acid sequence selected from amino acid sequence of SEQ ID NO: 76. Specifically, the present invention provides peptides comprising an amino acid sequence selected from the group of SEQ ID NOs: 3, 4, 9, 23, 25, 30, 60, 63 and 68, and which have CTL inducibility. The peptides of the invention encompass those wherein one, two or more amino acids are substituted or added, so long as the modified peptides retain the original CTL inducibility.

When administered to a subject, the present peptides are presented on the surface of antigen-expressing cells and then induce CTLs targeting the respective peptides. Therefore, according to an aspect of the present invention, antigen-presenting cells and exosomes which present any of the present peptides, as well as methods for inducing antigen-presenting cells are also provided.

An anti-tumor immune response is induced by the administration of the present TEM8 polypeptides or polynucleotide encoding the polypeptides, as well as exosomes and antigen-presenting cells which present the TEM8 polypeptides. Therefore, the present invention provides pharmaceutical agents containing the polypeptides or polynucleotides encoding them, as well as the exosomes and antigen-presenting cells as their active ingredients. The pharmaceutical agents of the present invention find use as vaccines.

Moreover, the present invention provides methods for treating and/or prophylaxis of (i.e., preventing) cancers (tumors), and/or prevention of postoperative recurrence thereof, as well as methods for inducing CTLs, methods for inducing an immune response against tumor-associated endothelia and also anti-tumor immunity, which methods comprise the step of administering the TEM8 polypeptides, polynucleotides encoding TEM8 polypeptides, exosomes or the antigen-presenting cells presenting TEM8 polypeptides or the pharmaceutical agents of the invention.

In addition, CTLs that target the present TEM polypeptides strengthen the immune responses targeting tumor-associated endothelium. Therefore, the present invention provides CTLs that target the present TEM polypeptides. The CTLs of the invention also find use as vaccines against cancer.

It is to be understood that both the foregoing summary of the invention and the following detailed description are of exemplified embodiments, and not restrictive of the invention or other alternate embodiments of the invention.

DETAILED DESCRIPTION OF THE INVENTION

I. Definitions

Figure 1:
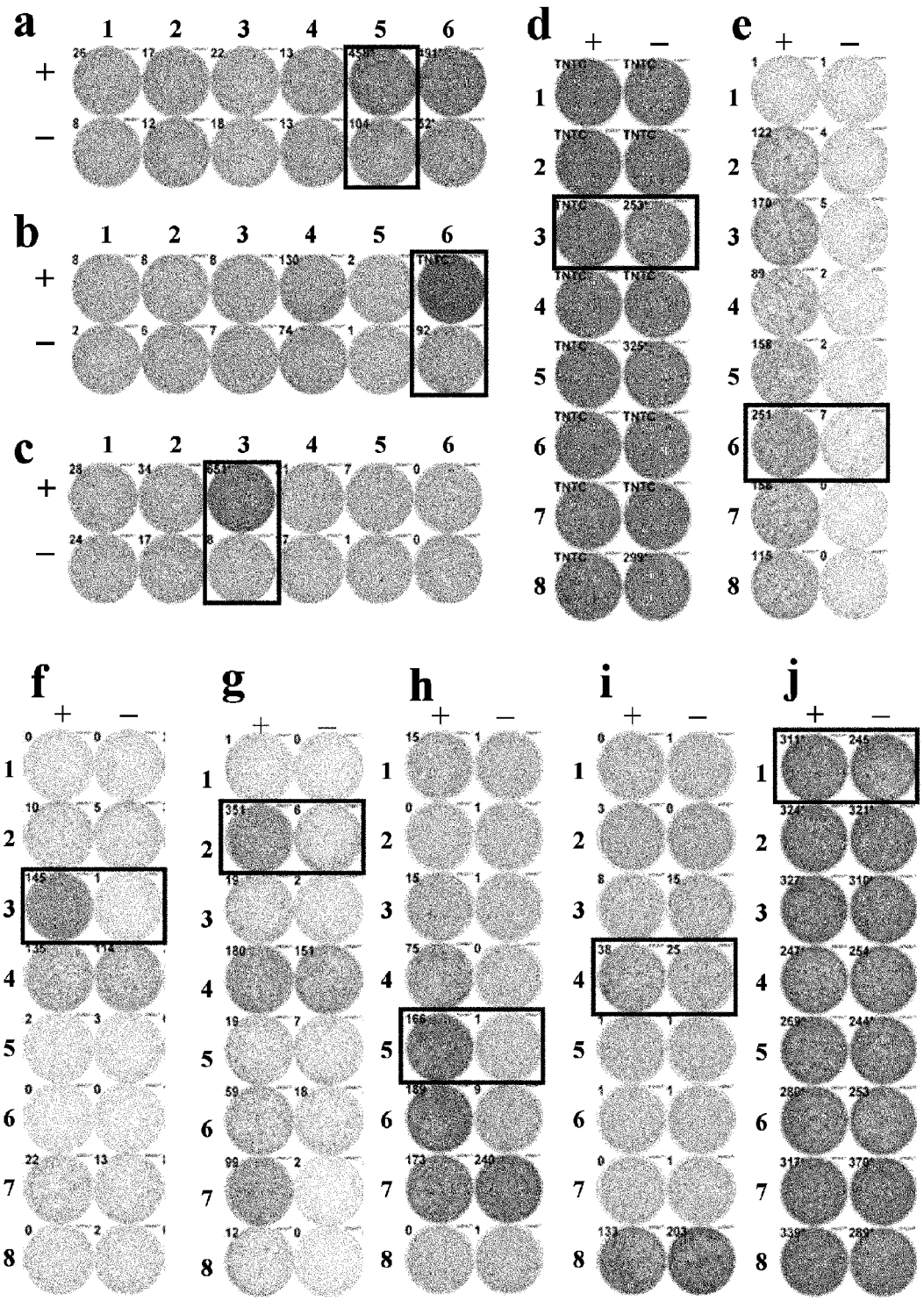
FIG. 1 depicts photographs showing the results of IFN-gamma ELISPOT assay on CTLs that were induced with peptides derived from TEM8. The CTLs in the well numbers #5 and #6 stimulated with TEM8-A24-9-39 (SEQ ID NO:3) (a), #6 with TEM8-A24-9-277 (SEQ ID NO:4) (b), #3 with TEM8-A24-10-277 (SEQ ID NO:9) (c), #3 with TEM8-A02-9-337 (SEQ ID NO: 23) (d), #6 with TEM8-A02-9-338 (SEQ ID NO: 25) (e), #3 with TEM8-A02-9-278 (SEQ ID NO: 30) (f), #2 with TEM8-A02-10-338 (SEQ ID NO: 60) (g), #5 with TEM8-A02-10-265 (SEQ ID NO: 63) (h) and #4 with TEM8-A02-10-333 (SEQ ID NO: 68) (i) showed potent IFN-gamma production compared with the control respectively. In contrast, as typical case of negative data (no CTL-induction), it was not shown specific IFN-gamma production from the CTL stimulated with TEM8-A02-9-207 (SEQ ID NO: 46) against peptide-pulsed target cells (j). Most of the predicted peptides showed no CTL-induction, therefore the positive data (CTL-induction) was focused upon in this invention. The square on the well of these pictures indicated that the cells from corresponding well were expanded to establish CTL lines. In the figures, "+" indicated the IFN-gamma production against target cells pulsed with the appropriate peptide, and "−" indicated the IFN-gamma production against target cells not pulsed with any peptides.
Figure 2:
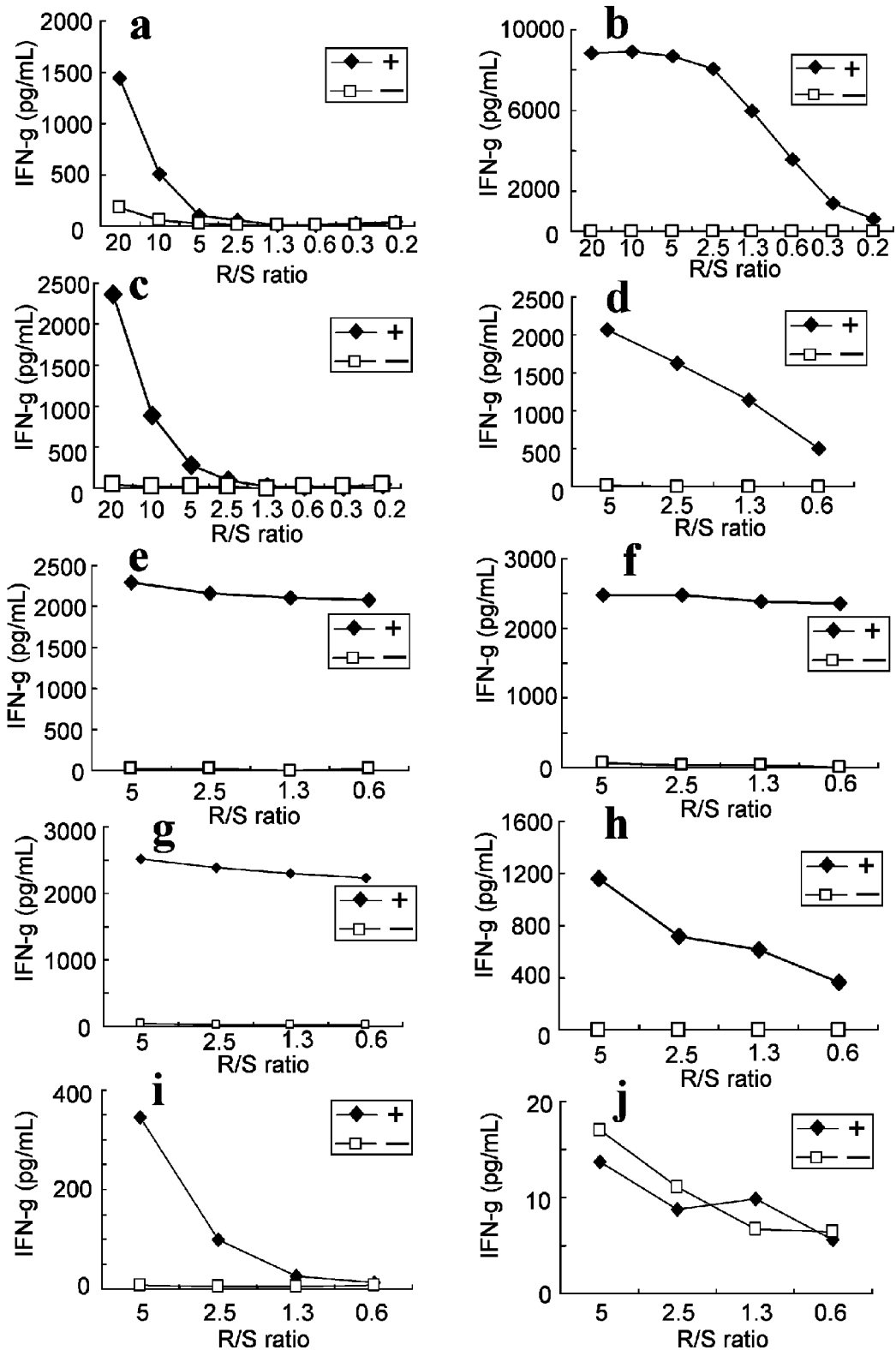
FIG. 2 depicts line graphs showing the results of establishment of CTL lines stimulated with TEM8-A24-9-39 (SEQ ID NO:3) (a), TEM8-A24-9-277 (SEQ ID NO:4) (b), TEM8-A24-10-277 (SEQ ID NO:9) (c), TEM8-A02-9-337 (SEQ ID NO: 23) (d), TEM8-A02-9-338 (SEQ ID NO: 25) (e), TEM8-A02-9-278 (SEQ ID NO: 30) (f), TEM8-A02-10-338 (SEQ ID NO: 60) (g), TEM8-A02-10-265 (SEQ ID NO: 63) (h) and TEM8-A02-10-333 (SEQ ID NO: 68) (i) with IFN-gamma ELISA assay. It demonstrated that CTL lines established by stimulation with each peptide showed potent IFN-gamma production compared with the control. In contrast, as typical case of negative data, it was not shown specific IFN-gamma production from the CTL line established with TEM8-A02-9-207 (SEQ ID NO: 46) against peptide-pulsed target cells (j). In the figures, "+" indicated the IFN-gamma production against target cells pulsed with the appropriate peptide, and "−" indicated the IFN-gamma production against target cells not pulsed with any peptides.

The words "a", "an", and "the" as used herein mean "at least one" unless otherwise specifically indicated.

The terms "polypeptide", "peptide" and "protein" are used interchangeably herein to refer to a polymer of amino acid residues. The terms apply to amino acid polymers in which one or more amino acid residue is a modified residue, or a non-naturally occurring residue, such as an artificial chemical mimetic of a corresponding naturally occurring amino acid, as well as to naturally occurring amino acid polymers.

The term "amino acid" as used herein refers to naturally occurring and synthetic amino acids, as well as amino acid analogs and amino acid mimetics that similarly function to the naturally occurring amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have a modified R group or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "gene", "polynucleotides", "nucleotides" and "nucleic acids" are used interchangeably herein unless otherwise specifically indicated and are similarly to the amino acids referred to by their commonly accepted single-letter codes.

Unless otherwise defined, all technical and scientific terms used herein have the same meaning as commonly understood by one of ordinary skill in the art to which this invention belongs.

II. Peptides

To demonstrate that peptides derived from TEM8 function as an antigen recognized by cytotoxic T lymphocytes (CTLs), peptides derived from TEM8 (GenBank Accession No. NP_115584 (SEQ ID NO: 76)) were analyzed to determine whether they were antigen epitopes restricted by HLA-A24 or HLA-A02 which are commonly encountered HLA alleles (Date Y et al., Tissue Antigens 47: 93-101, 1996; Kondo A et al., J Immunol 155: 4307-12, 1995; Kubo R T et al., J Immunol 152: 3913-24, 1994). Candidates of HLA-A24 and HLA-A02 binding peptides derived from TEM8 were identified using the information on their binding affinities to HLA-A24 and HLA-A02. After in vitro stimulation of T-cells by dendritic cells (DCs) loaded with these peptides, CTLs were successfully established using each of the following peptides.
TEM8-A24-9-39 (SEQ ID NO: 3),
TEM8-A24-9-277 (SEQ ID NO: 4),
TEM8-A24-10-277 (SEQ ID NO: 9),
TEM8-A02-9-337 (SEQ ID NO: 23),
TEM8-A02-9-338 (SEQ ID NO: 25),
TEM8-A02-9-278 (SEQ ID NO: 30),
TEM8-A02-10-338 (SEQ ID NO: 60),
TEM8-A02-10-265 (SEQ ID NO: 63) and
TEM8-A02-10-333 (SEQ ID NO: 68).

These established CTLs showed potent specific CTL activity against target cells pulsed with respective peptides. These results demonstrate that TEM8 is an antigen recognized by CTL and that the following peptides are epitope peptides of TEM8 restricted by HLA-A24 or HLA-A02.
TEM8-A24-9-39 (SEQ ID NO: 3),
TEM8-A24-9-277 (SEQ ID NO: 4),
TEM8-A24-10-277 (SEQ ID NO: 9),
TEM8-A02-9-337 (SEQ ID NO: 23),
TEM8-A02-9-338 (SEQ ID NO: 25),
TEM8-A02-9-278 (SEQ ID NO: 30),
TEM8-A02-10-338 (SEQ ID NO: 60),
TEM8-A02-10-265 (SEQ ID NO: 63) and
TEM8-A02-10-333 (SEQ ID NO: 68).

Since the TEM8 gene is over expressed in most cancer patients, it is a good target for immunotherapy with enhanced clinical efficacy. Thus, the present invention provides nonapeptides (peptides consisting of nine amino acid residues) and decapeptides (peptides consisting of ten amino acid residues) of CTL-recognized epitopes from TEM8. In the present invention, amino acid sequences of nonapeptides or decapeptides may be selected from SEQ ID NO:76. Thus, present invention provides an isolated peptide having cytotoxic T cell inducibility, wherein the peptide comprises nine or ten contiguous amino acid sequence selected from the amino acid sequence of SEQ ID NO:76. More specifically, in some embodiments, the invention provides peptides consisting of the amino acid sequence selected from the group of SEQ ID NOs: 3, 4, 9, 23, 25, 30, 60, 63 and 68.

Generally, software programs now available on the Internet, such as those described in Parker K C et al., J Immunol 1994 Jan. 1, 152(1): 163-75, can be used to calculate the binding affinities between various peptides and HLA antigens in silico. Binding affinity with HLA antigens can be measured as described, for example, in Parker K C et al., J Immunol 1994 Jan. 1, 152(1): 163-75; and Kuzushima K et al., Blood 2001, 98(6): 1872-81. The methods for determining binding affinity is described, for example, in; Journal of Immunological Methods, 1995, 185: 181-190; Protein Science, 2000, 9: 1838-1846. Thus, the present invention encompasses peptides of TEM8 which are determined to bind with HLA antigens by such known programs.

Furthermore, these peptides of the present invention can be flanked with additional amino acid residues so long as the peptide retains its CTL inducibility. Such peptides with CTL inducibility are for example, less than about 40 amino acids, often less than about 20 amino acids, usually less than about 15 amino acids. The amino acid sequence flanking the peptides consisting of the amino acid sequence selected from the group of SEQ ID NOs: 3, 4, 9, 23, 25, 30, 60, 63 and 68 is not limited and can be composed of any kind of amino acids so long as it does not impair the CTL inducibility of the original peptide. Thus, the present invention also provides peptides having CTL inducibility, which comprises the amino acid sequence selected from the group of SEQ ID NOs: 3, 4, 9, 23, 25, 30, 60, 63 and 68.

Generally, it is known that modifications of one or more amino acid in a protein do not influence the function of the protein, or in some cases even enhance the desired function of the original protein. In fact, modified peptides (i.e., peptides composed of an amino acid sequence modified by substituting or adding one, two or several amino acid residues to an original reference sequence) have been known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, according to one embodiment of the invention, the peptide having CTL inducibility of the present invention can be composed of the amino acids comprising the amino acid sequence of SEQ ID NO: 3, 4, 9, 23, 25, 30, 60, 63 or 68, wherein one, two or even more amino acids are added and/or substituted.

One of skill in the art will recognize that individual additions or substitutions to an amino acid sequence which alters a single amino acid or a small percentage of amino acids results in the conservation of the properties of the original amino acid side-chain; it is thus referred to as "conservative substitution" or "conservative modification", wherein the alteration of a protein results in a protein with similar functions. Conservative substitution tables providing functionally similar amino acids are well known in the art. Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are conservative substitutions for one another:

(1) Alanine (A), Glycine (G);
(2) Aspartic acid (D), Glutamic acid (E);
(3) Asparagine (N), Glutamine (Q);
(4) Arginine (R), Lysine (K);
(5) Isoleucine (I), Leucine (L), Methionine (M), Valine (V);
(6) Phenylalanine (F), Tyrosine (Y), Tryptophan (W);
(7) Serine (S), Threonine (T); and
(8) Cysteine (C), Methionine (M) (see, e.g., Creighton, Proteins 1984).

Such conservatively modified peptides are also considered to be peptides of the present invention. However, the peptide of the present invention is not restricted thereto and can include non-conservative modifications, so long as the peptide retains the CTL inducibility. Furthermore, the modified peptides do not exclude CTL inducible peptides of polymorphic variants, interspecies homologues, and alleles of TEM8.

To retain the requisite CTL inducibility one can modify (add or substitute) a small number (for example, 1, 2 or several) or a small percentage of amino acids. Herein, the term "several" means 5 or fewer amino acids, for example, 3 or fewer. The percentage of amino acids to be modified can be 20% or less, for example, 15% of less, for example 10% or 1 to 5%.

Homology analysis of the present peptides, TEM8-A24-9-39 (SEQ ID NO: 3), TEM8-A24-9-277 (SEQ ID NO: 4), TEM8-A24-10-277 (SEQ ID NO: 9), TEM8-A02-9-337 (SEQ ID NO: 23), TEM8-A02-9-338 (SEQ ID NO: 25), TEM8-A02-9-278 (SEQ ID NO: 30), TEM8-A02-10-338 (SEQ ID NO: 60), TEM8-A02-10-265 (SEQ ID NO: 63) and TEM8-A02-10-333 (SEQ ID NO: 68) showed that they do not have significant homology with peptides derived from any other known human gene products. This lowers the possibility of unknown or undesired immune responses when used for immunotherapy. Therefore, also from this aspect, these peptides find use for eliciting immunity in tumor patients against TEM8 on tumor-associated endothelium.

When used in immunotherapy, the present peptides are presented on the surface of a cell or exosome as a complex with an HLA antigen. Therefore, one can select peptides that possess high binding affinity to the HLA antigen in addition to their CTL inducibility. Moreover, the peptides can be modified by substitution, addition and such of the amino acid residues to achieve a higher binding affinity. In addition to peptides that are naturally displayed, since the regularity of the sequences of peptides displayed by binding to HLA antigens is already known (J Immunol 1994, 152: 3913; Immunogenetics 1995, 41: 178; J Immunol 1994, 155: 4307), modifications based on such regularity can be introduced into the immunogenic peptides of the invention. For example, peptides showing high HLA-A24 binding affinity have their second amino acid from the N-terminus substituted with phenylalanine, tyrosine, methionine, or tryptophan, and peptides whose amino acid at the C-terminus is substituted with phenylalanine, leucine, isoleucine, tryptophan, or methionine can also be favorably used. Thus, peptides having the amino acid sequences of SEQ ID NOs: 3, 4 or 9 wherein the second amino acid from the N-terminus is substituted with phenylalanine, tyrosine, methionine, or tryptophan, and peptides, and/or wherein the C-terminus is substituted with phenylalanine, leucine, isoleucine, tryptophan, or methionine are encompassed by the present invention.

On the other hand, peptides which second amino acid from the N-terminus is substituted with leucine or methionine, and in which the C-terminal amino acid is substituted with valine or leucine can be used as peptides with high HLA-02 binding affinity. Thus, peptides having any of the amino acid sequences SEQ ID NO: 23, 25, 30, 60, 63 and 68 wherein the second amino acid from the N-terminus is substituted with leucine or methionine, and/or wherein the C-terminus is substituted with valine or leucine are encompassed by the present invention. Substitutions can be introduced not only at the terminal amino acids but also at the position of potential TCR recognition of peptides. Several studies have demonstrated that amino acid substitutions in a peptide can be equal to or better than the original, for example CAP1, $p53_{(264-272)}$, Her-2/neu$_{(369-377)}$ or gp100$_{(209-217)}$ (Zaremba et al. Cancer Res. 57, 4570-4577, 1997, T. K. Hoffmann et al. J. Immunol. (2002) Feb. 1; 168(3):1338-47., S. O. Dionne et al. Cancer Immunol immunother. (2003) 52: 199-206 and S. O. Dionne et al. Cancer Immunology, Immunotherapy (2004) 53, 307-314).

Furthermore, one to two amino acids can also be added to the N and/or C-terminus of the present peptides. Such modified peptides with high HLA antigen binding affinity and retained CTL inducibility are also included in the present invention.

However, when the peptide sequence is identical to a portion of the amino acid sequence of an endogenous or exogenous protein having a different function, side effects such as autoimmune disorders or allergic symptoms against specific substances may be induced. Therefore, one can perform homology searches using available databases to avoid situations in which the sequence of the peptide matches the amino acid sequence of another protein. When it becomes clear from the homology searches that there exists not even a peptide with 1 or 2 amino acids difference to the objective peptide, the objective peptide can be modified in order to increase its binding affinity with HLA antigens, and/or increase its CTL inducibility without any danger of such side effects.

Although peptides having high binding affinity to the HLA antigens as described above are expected to be highly effective, the candidate peptides, which are selected according to the presence of high binding affinity as an indicator, are further examined for the presence of CTL inducibility. Herein, the phrase "CTL inducibility" indicates the ability of the peptide to induce CTLs when presented on antigen-presenting cells. Further, "CTL inducibility" includes the ability of the peptide to induce CTL activation, CTL proliferation, promote CTL lysis of target cells, and to increase CTL IFN-gamma production.

Confirmation of CTL inducibility is accomplished by inducing antigen-presenting cells carrying human MHC antigens (for example, B-lymphocytes, macrophages, and dendritic cells (DCs)), or more specifically DCs derived from human peripheral blood mononuclear leukocytes, and after stimulation with the peptides, mixing with CD8-positive cells, and then measuring the IFN-gamma produced and released by CTL against the target cells. As the reaction system, transgenic animals that have been produced to express a human HLA antigen (for example, those described in BenMohamed L, Krishnan R, Longmate J, Auge C, Low L, Primus J, Diamond D J, Hum Immunol 2000 August, 61(8): 764-79, Related Articles, Books, Linkout Induction of CTL response by a minimal epitope vaccine in HLA A*0201/DR1 transgenic mice: dependence on HLA class II restricted T(H) response) can be used. For example, the target cells can be radiolabeled with $^{51}$Cr and such, and cytotoxic activity can be calculated from radioactivity released from the target cells. Alternatively, it can be examined by measuring IFN-gamma produced and released by CTL in the presence of antigen-presenting cells (APCs) that carry immobilized peptides, and visualizing the inhibition zone on the media using anti-IFN-gamma monoclonal antibodies.

As a result of examining the CTL inducibility of the peptides as described above, those having high binding affinity to an HLA antigen did not necessarily have high inducibility. Furthermore, nonapeptides or decapeptides selected from peptides comprising the amino acid sequences indicated by SEQ ID NOs: 3, 4, 9, 23, 25, 30, 60, 63 and 68, showed particularly high CTL inducibility as well as high binding affinity to an HLA antigen. Thus, these peptides are exemplified embodiments of the present invention.

In addition to modification of the present peptides, discussed above, the peptides of the present invention can be further linked to other substances, so long as they retain the CTL inducibility. Exemplified substances include: peptides, lipids, sugar and sugar chains, acetyl groups, natural and synthetic polymers, etc. The peptides can contain modifications such as glycosylation, side chain oxidation, or phosphorylation; so long as the modifications do not destroy the biological activity of the peptides as described herein. These kinds of modifications can be performed to confer additional functions (e.g., targeting function, and delivery function) or to stabilize the polypeptide.

For example, to increase the in vivo stability of a polypeptide, it is known in the art to introduce D-amino acids, amino acid mimetics or unnatural amino acids; this concept can also be adopted for the present polypeptides. The stability of a polypeptide can be assayed in a number of ways. For instance, peptidases and various biological media, such as human plasma and serum, can be used to test stability (see, e.g., Verhoef et al., Eur J Drug Metab Pharmacokin 1986, 11: 291-302).

Herein, the peptides of the present invention can also be described as "TEM8 peptide(s)" or "TEM8 polypeptide(s)".

III. Preparation of TEM8 Peptides

The peptides of the invention can be prepared using well known techniques. For example, the peptides can be prepared synthetically, by recombinant DNA technology or chemical synthesis. Peptide of the invention can be synthesized individually or as longer polypeptides comprising two or more peptides. The peptides can be isolated i.e., purified or isolated substantially free of other naturally occurring host cell proteins and fragments thereof, or any other chemical substances.

A peptide of the present invention can be obtained through chemical synthesis based on the selected amino acid sequence. For example, conventional peptide synthesis methods that can be adopted for the synthesis include:

(i) Peptide Synthesis, Interscience, New York, 1966;
(ii) The Proteins, Vol. 2, Academic Press, New York, 1976;
(iii) Peptide Synthesis (in Japanese), Maruzen Co., 1975;
(iv) Basics and Experiment of Peptide Synthesis (in Japanese), Maruzen Co., 1985;
(v) Development of Pharmaceuticals (second volume) (in Japanese), Vol. 14 (peptide synthesis), Hirokawa, 1991;
(vi) WO99/67288; and
(vii) Barany G. & Merrifield R. B., Peptides Vol. 2, "Solid Phase Peptide Synthesis", Academic Press, New York, 1980, 100-118.

Alternatively, the present peptides can be obtained adopting any known genetic engineering methods for producing peptides (e.g., Morrison J, J Bacteriology 1977, 132: 349-51; Clark-Curtiss & Curtiss, Methods in Enzymology (eds. Wu et al.) 1983, 101: 347-62). For example, first, a suitable vector harboring a polynucleotide encoding the objective peptide in an expressible form (e.g., downstream of a regulatory sequence corresponding to a promoter sequence) is prepared and transformed into a suitable host cell. The host cell is then cultured to produce the peptide of interest. The peptide can also be produced in vitro adopting an in vitro translation system.

IV. Polynucleotides

The present invention provides a polynucleotide which encodes any of the aforementioned peptides of the present invention. These include polynucleotides derived from the natural occurring TEM8 gene (GenBank Accession No. NM_032208 (SEQ ID NO: 75)) and those having a conservatively modified nucleotide sequence thereof. Herein, the phrase "conservatively modified nucleotide sequence" refers to sequences which encode identical or essentially identical amino acid sequences. Because of the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a peptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a peptide is implicitly described in each disclosed sequence.

The polynucleotide of the present invention can be composed of DNA, RNA, and derivatives thereof. A DNA is suitably composed of bases such as A, T, C, and G, and T is replaced by U in an RNA.

The polynucleotide of the present invention can encode multiple peptides of the present invention with or without intervening amino acid sequences in between. For example, the intervening amino acid sequence can provide a cleavage site (e.g., enzyme recognition sequence) of the polynucleotide or the translated peptides. Furthermore, the polynucleotide can include any additional sequences to the coding sequence encoding the peptide of the present invention. For example, the polynucleotide can be a recombinant polynucleotide that includes regulatory sequences required for the expression of the peptide or can be an expression vector (plasmid) with marker genes and such. In general, such recombinant polynucleotides can be prepared by the manipulation of polynucleotides through conventional recombinant techniques using, for example, polymerases and endonucleases.

Both recombinant and chemical synthesis techniques can be used to produce the polynucleotides of the present invention. For example, a polynucleotide can be produced by insertion into an appropriate vector, which can be expressed when transfected into a competent cell. Alternatively, a polynucleotide can be amplified using PCR techniques or expression in suitable hosts (see, e.g., Sambrook et al., Molecular Cloning: A Laboratory Manual, Cold Spring Harbor Laboratory, New York, 1989). Alternatively, a polynucleotide can be synthesized using the solid phase techniques, as described in Beaucage S L & Iyer R P, Tetrahedron 1992, 48: 2223-311; Matthes et al., EMBO J. 1984, 3: 801-5.

V. Exosomes

The present invention further provides intracellular vesicles called exosomes, which present complexes formed between the peptides of this invention and HLA antigens on their surface. Exosomes can be prepared, for example by using the methods detailed in Japanese Patent Application Kohyo Publications Nos. Hei 11-510507 and WO99/03499, and can be prepared using APCs obtained from patients who are subject to treatment and/or prevention. The exosomes of this invention can be inoculated as vaccines, similarly to the peptides of this invention.

The type of HLA antigens comprised in the complexes must match that of the subject requiring treatment and/or prevention. For example, for Japanese, HLA-A24, particularly HLA-A2402 is often appropriate. The use of A-24 or A-02 type that are highly expressed among the Japanese and Caucasian is favorable for obtaining effective results, and subtypes such as A-2402 and A-0201 find use. Typically, in the clinic, the type of HLA antigen of the patient requiring treatment is investigated in advance, which enables appropriate selection of peptides having high levels of binding affinity to this antigen, or having CTL inducibility by antigen presentation. Furthermore, in order to obtain peptides showing high binding affinity and CTL inducibility, substitution or addition of 1, 2, or several amino acids can be performed based on the amino acid sequence of the naturally occurring TEM8 partial peptide.

In case of using A-24 type HLA antigen for the exosome of the present invention, the peptides comprising the sequence of SEQ ID NO: 3, 4, or 9 find use, whereas in case of using A-02 type HLA antigen, those comprising the sequence of SEQ ID NO: 23, 25, 30, 60, 63 or 68 find use.

VI. Antigen-Presenting Cells (APCs)

The present invention also provides APCs that present complexes formed between HLA antigens and the peptides of this invention on its surface. The APCs that are obtained by contacting the peptides of this invention, or introducing the nucleotides encoding the peptides of this invention in an expressible form can be derived from patients who are subject to treatment and/or prevention, and can be administered as vaccines by themselves or in combination with other drugs including the peptides of this invention, exosomes, or cytotoxic T cells. Alternatively, the present invention also provides APCs presenting the peptide of the present invention with HLA antigens, wherein said APCs is induced by;
(a) contacting the peptides of the present invention with APCs, or
(b) introducing a polynucleotide encoding the peptides into APCs to produce the APCs.

The APCs are not limited to a particular kind of cells and include DCs, Langerhans cells, macrophages, B cells, and activated T cells, which are known to present proteinaceous antigens on their cell surface so as to be recognized by lymphocytes. Since DC is a representative APC having the strongest CTL inducing action among APCs, DCs find use as the APCs of the present invention.

For example, an APC can be obtained by inducing DCs from peripheral blood monocytes and then contacting (stimulating) them with the peptides of this invention in vitro, ex vivo or in vivo. When the peptides of this invention are administered to the subjects, APCs that present the peptides of this invention are induced in the body of the subject. "Inducing APC" includes contacting (stimulating) a cell with the peptides of this invention, or nucleotides encoding the peptides of this invention to present complexes formed between HLA antigens and the peptides of this invention on cell's surface. Alternatively, after introducing the peptides of this invention to the APCs to allow the APCs to present the peptides, the APCs can be administered to the subject as a vaccine. For example, the ex vivo administration can comprise steps of:
 a: collecting APCs from a first subject,
 b: contacting with the APCs of step a, with the peptide and
 c: administering the peptide-loaded APCs to a second subject.

The first subject and the second subject can be the same individual, or can be different individuals. Alternatively, according to the present invention, use of the peptides of this invention for manufacturing a pharmaceutical composition inducing antigen-presenting cells is provided. Further, the present invention also provides the peptides of the present invention for inducing antigen-presenting cells. The APCs obtained by step b can be administered to the subject as a vaccine.

According to an aspect of the present invention, the APCs have a high level of CTL inducibility. In the term of "high level of CTL inducibility", the high level is relative to the level of that by APC contacting with no peptide or peptides which can not induce the CTL. Such APCs having a high level of CTL inducibility can be prepared by a method which comprises the step of transferring genes comprising polynucleotides that encode the peptides of this invention to APCs in vitro. The introduced genes can be in the form of DNAs or RNAs. Examples of methods for introduction include, without particular limitations, various methods conventionally performed in this field, such as lipofection, electroporation, and calcium phosphate method can be used. More specifically, it can be performed as described in Cancer Res 1996, 56: 5672-7; J Immunol 1998, 161: 5607-13; J Exp Med 1996, 184: 465-72; Published Japanese Translation of International Publication No. 2000-509281. By transferring the gene into APCs, the gene undergoes transcription, translation, and such in the cell, and then the obtained protein is processed by MHC Class I or Class II, and proceeds through a presentation pathway to present partial peptides.

VII. Cytotoxic T Cells

A cytotoxic T cell induced against any of the peptides of the present invention strengthens the immune response targeting tumor-associated endothelia in vivo and thus can be used as vaccines similar to the peptides. Thus, the present invention provides isolated cytotoxic T cells that are specifically induced or activated by any of the present peptides. Preferably, the present invention provides an isolated cytotoxic T cell;

(a) that is induced by the step of contacting $CD^{8+}$ T cells with APCs presenting the peptides of the present invention with HLA antigens, or (b) which is transduced with the nucleic acids encoding the TCR subunits polypeptides binding with a peptide the present invention in the context of HLA-A24 or HLA-A2.

Such cytotoxic T cells can be obtained by (1) administering to a subject or (2) contacting (stimulating) subject-derived APCs, and CD8-positive cells, or peripheral blood mononuclear leukocytes in vitro with the peptides of the present invention.

The cytotoxic T cells, which have been induced by stimulation from APCs that present the peptides of this invention, can be derived from patients who are subject to treatment and/or prevention, and can be administered by themselves or in combination with other drugs including the peptides of this invention or exosomes for the purpose of regulating effects. The obtained cytotoxic T cells act specifically against target cells presenting the peptides of this invention, or for example, the same peptides used for induction. The target cells can be cells that endogenously express TEM8, or cells that are transfected with the TEM8 gene; and cells that present a peptide of this invention on the cell surface due to stimulation by the peptide can also serve as targets of activated CTL attack.

VIII. T Cell Receptor (TCR)

The present invention also provides a composition comprising nucleic acids encoding polypeptides that are capable of forming a subunit of a T cell receptor (TCR), and methods of using the same. The TCR subunits have the ability to form TCRs that confer specificity to T cells against tumor cells presenting TEM8. By using the known methods in the art, the nucleic acids of alpha- and beta-chains as the TCR subunits of the CTL induced with one or more peptides of this invention can be identified (WO2007/032255 and Morgan et al., J Immunol, 171, 3288 (2003)). The derivative TCRs can bind target cells displaying the TEM8 peptide with high avidity, and optionally mediate efficient killing of target cells presenting the TEM8 peptide in vivo and in vitro.

The nucleic acids encoding the TCR subunits can be incorporated into suitable vectors e.g. retroviral vectors. These vectors are well known in the art. The nucleic acids or the vectors comprising them usefully can be transferred into a T cell, for example, a T cell from a patient. Advantageously, the invention provides an off-the-shelf composition allowing rapid modification of a patient's own T cells (or those of another mammal) to rapidly and easily produce modified T cells having excellent cancer cell killing properties.

Also, the present invention provides CTLs which are prepared by transduction with the nucleic acids encoding the TCR subunits polypeptides that bind to the TEM8 peptide e.g. SEQ ID NOs: 3, 4, 9, 23, 25, 30, 60, 63 and 68 in the context of HLA-A24 or HLA-A2. The transduced CTLs are capable of homing to cancer cells in vivo, and can be expanded by well known culturing methods in vitro (e.g., Kawakami et al., J Immunol., 142, 3452-3461 (1989)). The T cells of the invention can be used to form an immunogenic composition useful in treating or the prevention of cancer in a patient in need of therapy or protection (WO2006/031221).

Prevention and prophylaxis include any activity which reduces the burden of mortality or morbidity from disease. Prevention and prophylaxis can occur "at primary, secondary and tertiary prevention levels." While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis include a wide range of prophylactic therapies aimed at alleviating the severity of the particular disorder, e.g. reducing the proliferation and metastasis of tumors, reducing angiogenesis.

Treating and/or for the prophylaxis of cancer or, and/or the prevention of postoperative recurrence thereof includes any of the following steps, such as surgical removal of cancer cells, inhibition of the growth of cancerous cells, involution or regression of a tumor, induction of remission and suppression of occurrence of cancer, tumor regression, and reduction or inhibition of metastasis. Effectively treating and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effectively treating and/or the prophylaxis include 10%, 20%, 30% or more reduction, or stable disease.

IX. Pharmaceutical Agents

Since TEM8 expression is specifically elevated in tumor-associated endothelium compared with normal tissue (St Croix B et al., Science 2000 Aug. 18, 289(5482): 1197-202), the peptides of this invention or polynucleotides encoding the peptides can be used for treating and/or for the prophylaxis of cancer, and/or prevention of postoperative recurrence thereof. Thus, the present invention provides a pharmaceutical agent for treating and/or for the prophylaxis of cancer, and/or prevention of postoperative recurrence thereof, which comprises one or more of the peptides of this invention, or polynucleotides encoding the peptides as an active ingredient. Alternatively, the present peptides can be expressed on the surface of any of the foregoing exosomes or cells, such as APCs for the use as pharmaceutical agents. In addition, the aforementioned cytotoxic T cells which target any of the peptides of the invention can also be used as the active ingredient of the present pharmaceutical agents.

The present pharmaceutical agents find use as a vaccine. In the present invention, the phrase "vaccine" (also referred to as an immunogenic composition) refers to a substance that has the function to induce anti-tumor immunity upon inoculation into animals.

The pharmaceutical agents of the present invention can be used to treat and/or prevent cancers, and/or prevention of postoperative recurrence thereof in subjects or patients including human and any other mammal including, but not limited to, mouse, rat, guinea-pig, rabbit, cat, dog, sheep, goat, pig, cattle, horse, monkey, baboon, and chimpanzee, particularly a commercially important animal or a domesticated animal.

According to the present invention, polypeptides comprising the amino acid sequence of SEQ ID NO: 3, 4 or 9 have been found to be HLA-A24 restricted epitope peptides that can induce potent and specific immune response against tumor-associated endothelium. Therefore, the present pharmaceutical agents which comprise any of these polypeptides with the amino acid sequences of SEQ ID NOs: 3, 4 and 9 are particularly suited for the administration to subjects whose HLA antigen is HLA-A24. On the other hand, the polypeptides comprising the amino acid sequence of SEQ ID NO: 23, 25, 30, 60, 63 or 68 have been found to be HLA-A02 restricted epitope peptides that can induce potent and specific immune response against tumor-associated endothelium. Therefore, the pharmaceutical agents which comprise any of these polypeptides that comprise any of these polypeptides with the amino acid sequences of SEQ ID NOs: 23, 25, 30, 60, 63 and 68 are particularly suited for the administration to subjects whose HLA antigen is HLA-A02. The same applies to pharmaceutical agents which comprise polynucleotides encoding any of these polypeptides.

Figure 5:
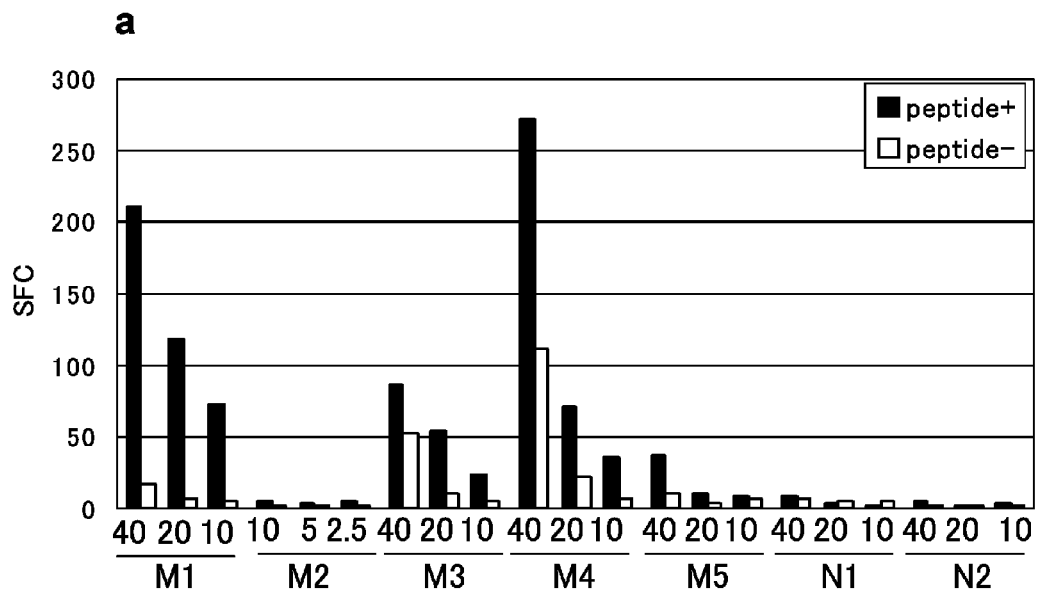
FIG. 5 depicts in vivo immunogenicity and antitumor effects of vaccination using TEM8-A24-9-277 peptide. (a) In vivo immunogenicity of TEM8 epitope peptide was examined according to the protocol as described in "Materials and Methods". BALB/c mice were injected with Incomplete Freund's adjuvant (IFA)-conjugated TEM8-A24-9-277 (SEQ ID NO: 4) (M1-M5) or IFA only (N1 and N2). In the figures, "+" indicated the IFN-gamma production against target cells pulsed with peptide (black bar), and "−" indicated the IFN-gamma production against target cells not pulsed with any peptides (white bar). Splenocytes from the vaccinated mice produced IFN-gamma against RLmale1 cells pulsed with TEM8-A24-9-277 (SEQ ID NO: 4) without producing it against target cells not pulsed with any peptides. SFC indicated spot forming cells. (b) Antitumor effects by vaccination using TEM8 epitope peptide was tested as preventive setting. IFA-conjugated with TEM8-A24-9-277 (SEQ ID NO: 4) (black triangular mark) or no peptide (open lozenge-mark) was injected on day −7 and 0 into BALB/c mice. 5×10⁴ CT26, mouse colorectal cancer cell lines, were injected s.c. into vaccinated mice on day 0. Tumor sizes are represented as the mean of five mice. Significant difference of tumor growth suppression was observed by the vaccination of epitope peptide (*; P<0.05).
Figure 5:
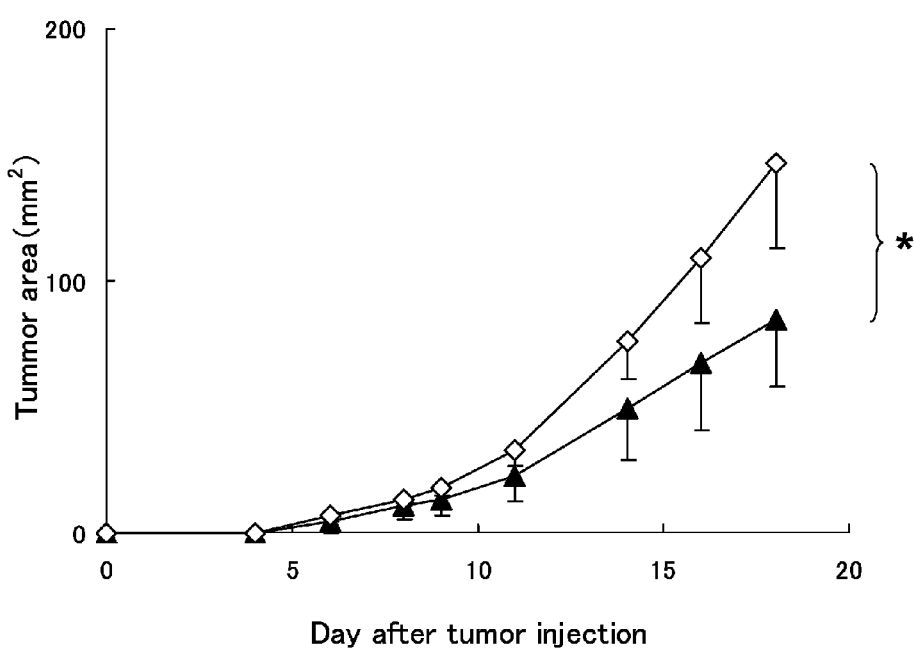

Cancers to be treated by the pharmaceutical agents of the present invention are not limited and include all kinds of cancers wherein TEM8 is involved, including for example, bladder cancer, brain cancer, breast cancer, cervical, cholangiocellular carcinoma, endometriosis, esophagus, gastric, liver cancer, lung cancer, neuroblastoma, osteosarcoma, ovarian, melanoma, pancreatic cancer, prostate cancer, renal cancer, testicular tumor or colorectal cancer (see FIG. 5).

The present pharmaceutical agents can contain in addition to the aforementioned active ingredients, other peptides which have the ability to induce CTLs against cancerous cells, other polynucleotides encoding the other peptides, other cells that present the other peptides, or such. Herein, the other peptides that have the ability to induce CTLs against cancerous cells are exemplified by cancer specific antigens (e.g., identified TAAs), but are not limited thereto.

If needed, the pharmaceutical agents of the present invention can optionally include other therapeutic substances as an active ingredient, so long as the substance does not inhibit the antitumoral effect on tumor-associated endothelium of the active ingredient, e.g., any of the present peptides. For example, formulations can include anti-inflammatory agents, pain killers, chemotherapeutics, and the like. In addition to including other therapeutic substances in the medicament itself, the medicaments of the present invention can also be administered sequentially or concurrently with the one or more other pharmacologic agents. The amounts of medicament and pharmacologic agent depend, for example, on what type of pharmacologic agent(s) is/are used, the disease being treated, and the scheduling and routes of administration.

It should be understood that in addition to the ingredients particularly mentioned herein, the pharmaceutical agents of this invention can include other agents conventional in the art having regard to the type of formulation in question.

In one embodiment of the present invention, the present pharmaceutical agents can be included in articles of manufacture and kits containing materials useful for treating the pathological conditions of the disease to be treated, e.g, cancer. The article of manufacture can include a container of any of the present pharmaceutical agents with a label. Suitable containers include bottles, vials, and test tubes. The containers can be formed from a variety of materials, such as glass or plastic. The label on the container should indicate the agent is used for treating or prevention of one or more conditions of the disease. The label can also indicate directions for administration and so on.

In addition to the container described above, a kit including a pharmaceutical agent of the present invention can optionally further include a second container housing a pharmaceutically-acceptable diluent. It can further include other materials desirable from a commercial and user standpoint, including other buffers, diluents, filters, needles, syringes, and package inserts with instructions for use.

The pharmaceutical compositions can, if desired, be presented in a pack or dispenser device which can contain one or more unit dosage forms containing the active ingredient. The pack can, for example, include metal or plastic foil, such as a blister pack. The pack or dispenser device can be accompanied by instructions for administration.

(1) Pharmaceutical Agents Containing the Peptides as the Active Ingredient

The peptides of this invention can be administered directly as a pharmaceutical agent, or if necessary, that has been formulated by conventional formulation methods. In the latter case, in addition to the peptides of this invention, carriers, excipients, and such that are ordinarily used for drugs can be included as appropriate without particular limitations. Examples of such carriers are sterilized water, physiological saline, phosphate buffer, culture fluid and such. Furthermore, the pharmaceutical agents can contain as necessary, stabilizers, suspensions, preservatives, surfactants and such. The pharmaceutical agents of this invention can be used for anticancer purposes.

The peptides of this invention can be prepared in a combination, which comprises two or more of peptides of the invention, to induce CTL in vivo. The peptides can be in a cocktail or can be conjugated to each other using standard techniques. For example, the peptides can be chemically linked or expressed as a single fusion polypeptide sequence. The peptides in the combination can be the same or different. By administering the peptides of this invention, the peptides are presented at a high density by the HLA antigens on APCs, then CTLs that specifically react toward the complex formed between the displayed peptide and the HLA antigen are induced. Alternatively, APCs that present any of the peptides of this invention on their cell surface are obtained by removing APCs (e.g., DCs) from the subjects, which are stimulated by the peptides of this invention, CTL is induced in the subjects by readministering these APCs (e.g., DCs) to the subjects, and as a result, aggressiveness towards the tumor-associated endothelium can be increased.

The pharmaceutical agents for treating and/or prevention of cancer, which comprise a peptide of this invention as the active ingredient, can comprise an adjuvant so that cellular immunity will be established effectively, or they can be administered with other active ingredients, and they can be administered by formulation into granules. An adjuvant refers to a compound that enhances the immune response against the protein when administered together (or successively) with the protein having immunological activity. An adjuvant that can be applied includes those described in the literature (Clin Microbiol Rev 1994, 7: 277-89). Exemplary adjuvants include aluminum phosphate, aluminum hydroxide, alum, cholera toxin, *salmonella* toxin, and such, but are not limited thereto.

Furthermore, liposome formulations, granular formulations in which the peptide is bound to few-micrometers diameter beads, and formulations in which a lipid is bound to the peptide may be conveniently used.

In some embodiments, the pharmaceutical agents of the invention comprise a component which primes CTL. Lipids have been identified as agents capable of priming CTL in vivo against viral antigens. For example, palmitic acid residues can be attached to the epsilon- and alpha-amino groups of a lysine residue and then linked to a peptide of the invention. The lipidated peptide can then be administered either directly in a micelle or particle, incorporated into a liposome, or emulsified in an adjuvant. As another example of lipid priming of CTL responses, *E. coli* lipoproteins, such as tripalmitoyl-S-glycerylcysteinlyseryl-serine (P3CSS) can be used to prime CTL when covalently attached to an appropriate peptide (see, e.g., Deres et al., Nature 1989, 342: 561-4).

The method of administration can be oral, intradermal, subcutaneous, intravenous injection, or such, and systemic administration or local administration to the vicinity of the targeted sites. The administration can be performed by single administration or boosted by multiple administrations. The dose of the peptides of this invention can be adjusted appropriately according to the disease to be treated, age of the patient, weight, method of administration, and such, and is ordinarily 0.001 mg to 1000 mg, for example, 0.001 mg to 1000 mg, for example, 0.1 mg to 10 mg, and can be administered once in a few days to few months. One skilled in the art can appropriately select a suitable dose.

(2) Pharmaceutical Agents Containing Polynucleotides as the Active Ingredient

The pharmaceutical agents of the invention can also comprise nucleic acids encoding the peptides disclosed herein in an expressible form. Herein, the phrase "in an expressible form" means that the polynucleotide, when introduced into a cell, will be expressed in vivo as a polypeptide that induces anti-tumor immunity. In an exemplified embodiment, the nucleic acid sequence of the polynucleotide of interest includes regulatory elements necessary for expression of the polynucleotide. The polynucleotide(s) can be equipped so to achieve stable insertion into the genome of the target cell (see, e.g., Thomas K R & Capecchi M R, Cell 1987, 51: 503-12 for a description of homologous recombination cassette vectors). See, e.g., Wolff et al., Science 1990, 247: 1465-8; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The peptides of the invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 1991, 351: 456-60. A wide variety of other vectors useful for therapeutic administration or immunization e.g., adeno and adeno-associated virus vectors, retroviral vectors, *Salmonella typhi* vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide into a patient can be either direct, in which case the patient is directly exposed to a polynucleotide-carrying vector, or indirect, in which case, cells are first transformed with the polynucleotide of interest in vitro, then the cells are transplanted into the patient. Theses two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215). Methods commonly known in the art of recombinant DNA technology which can also be used for the present invention are described in eds. Ausubel et al., Current Protocols in Molecular Biology, John Wiley & Sons, NY, 1993; and Krieger, Gene Transfer and Expression, A Laboratory Manual, Stockton Press, NY, 1990.

The method of administration can be oral, intradermal, subcutaneous, intravenous injection, or such, and systemic administration or local administration to the vicinity of the targeted sites finds use. The administration can be performed by single administration or boosted by multiple administrations. The dose of the polynucleotide in the suitable carrier or cells transformed with the polynucleotide encoding the peptides of this invention can be adjusted appropriately according to the disease to be treated, age of the patient, weight, method of administration, and such, and is ordinarily 0.001 mg to 1000 mg, for example, 0.001 mg to 1000 mg, for example, 0.1 mg to 10 mg, and can be administered once every a few days to once every few months. One skilled in the art can appropriately select the suitable dose.

X. Methods Using the Peptides, Exosomes, APCs and CTLs

The peptides of the present invention and polynucleotides encoding the peptides can be used for inducing APCs and CTLs. The exosomes and APCs of the present invention can be also used for inducing CTLs. The peptides, polynucleotides, exosomes and APCs can be used in combination with any other compounds so long as the compounds do not inhibit their CTL inducibility. Thus, any of the aforementioned pharmaceutical agents of the present invention can be used for inducing CTLs, and in addition thereto, those comprising the peptides and polynucleotides can be also be used for inducing APCs as explained below.

(1) Method of Inducing Antigen-Presenting Cells (APCs)

The present invention provides methods of inducing APCs using the peptides of this invention or polynulceotides encoding the peptides. The induction of APCs can be performed as described above in section "VI. Antigen-presenting cells". This invention also provides a method for inducing APCs having a high level of CTL inducibility, the induction of which has been also mentioned under the item of "VI. Antigen-presenting cells", supra. Preferably, the present invention provides a method for inducing APCs with high CTL inducibility, wherein the method comprises the step of contacting the peptides of the invention with APCs or introducing a polynucleotide encoding the peptides into APCs to produce the APCs presenting the peptide of the present invention with HLA antigens.

(2) Method of Inducing CTLs

Furthermore, the present invention provides methods for inducing CTLs using the peptides of this invention, polynucleotides encoding the peptides, or exosomes or APCs presenting the peptides. In a preferred embodiment, the method comprises the step of contacting $CD^{8+}$ T cells with;

(a) APCs presenting the peptides of the present invention with HLA antigens, or (b) APCs which is induced by introducing a gene that comprises a polynucleotide encoding the peptides of the present invention into an antigen-presenting cell. When the peptides of this invention are administered to a subject, CTL is induced in the body of the subject, and the strength of the immune response targeting the tumor-associated endothelia is enhanced. Alternatively, the peptides and polynucleotides encoding the peptides can be used for an ex vivo therapeutic method, in which subject-derived APCs, and CD8-positive cells, or peripheral blood mononuclear leukocytes are contacted (stimulated) with the peptides of this invention in vitro, and after inducing CTL, the activated CTL cells are returned to the subject. For example, the method can comprise steps of:

a: collecting APCs from subject:
b: contacting with the APCs of step a, with the peptide:
c: mixing the APCs of step b with $CD^{8+}$ T cells, and co-culturing for inducing CTLs: and
d: collecting $C^{8+}$ T cells from the co-culture of step c.

Alternatively, according to the present invention, use of the peptides of this invention for manufacturing a pharmaceutical composition inducing CTLs is provided. Further, the present invention also provides the peptide of the present invention for inducing CTLs.

The $CD^{8+}$ T cells having cytotoxic activity obtained by step d can be administered to the subject as a vaccine. The APCs to be mixed with the $CD^{8+}$ T cells in above step c can also be prepared by transferring genes coding for the present peptides into the APCs as detailed above in section "VI. Antigen-presenting cells"; but are not limited thereto and any APC or exosome which effectively presents the present peptides to the T cells can be used for the present method.

Although methods and materials similar or equivalent to those described herein can be used in the practice or testing of the present invention, suitable methods and materials are described. All publications, patent applications, patents, and other references mentioned herein are incorporated by reference in their entirety. In case of conflict, the present specification, including definitions, will control. In addition, the materials, methods, and examples are illustrative only and not intended to be limiting.

The following examples are presented to illustrate the present invention and to assist one of ordinary skill in making and using the same. The examples are not intended in any way to otherwise limit the scope of the invention.

EXAMPLES

Materials and Methods

Cell Lines

A24 lymphoblastoid cell line (A24LCL) cells were established by transformation with Epstein-bar virus into HLA-A24 positive human B lymphocyte. T2 (HLA-A2), human B-lymphoblastoid cell lines, COS7 and CT26, mouse colorectal cancer cell lines, were purchased from ATCC. RLmale1, mouse lymphoma cell lines, were purchased from Cell Resource Center for Biomedical Research, Tohoku University.

Candidate Selection of Peptides Derived from TEM8

9-mer and 10-mer peptides derived from TEM8 that bind to HLA-A*2402 and HLAA*0201 molecules were predicted using binding prediction software "BIMAS" (http://www-bimas.cit.nih.gov/molbio/hla_bind), which algorithms had been described by Parker K C et al. (J Immunol 1994, 152(1): 163-75) and Kuzushima K et al. (Blood 2001, 98(6): 1872-81). These peptides were synthesized by Sigma (Sapporo, Japan) according to a standard solid phase synthesis method and purified by reversed phase high performance liquid chromatography (HPLC). The purity (>90%) and the identity of the peptides were determined by analytical HPLC and mass spectrometry analysis, respectively. Peptides were dissolved in dimethylsulfoxide (DMSO) at 20 mg/ml and stored at −80 degrees C.

In Vitro CTL Induction

Monocyte-derived dendritic cells (DCs) were used as antigen-presenting cells (APCs) to induce cytotoxic T lymphocyte (CTL) responses against peptides presented on human leukocyte antigen (HLA). DCs were generated in vitro as described elsewhere (Nakahara S et al., Cancer Res 2003 Jul. 15, 63(14): 4112-8). Specifically, peripheral blood mononuclear cells (PBMCs) isolated from a normal volunteer (HLA-A*2402 or HLA-A*0201 positive) by Ficoll-Plaque (Pharmacia) solution were separated by adherence to a plastic tissue culture dish (Becton Dickinson) so as to enrich them as the monocyte fraction. The monocyte-enriched population was cultured in the presence of 1000 U/ml of granulocyte-macrophage colony-stimulating factor (GM-CSF) (R&D System) and 1000 U/ml of interleukin (IL)-4 (R&D System) in AIM-V Medium (Invitrogen) containing 2% heat-inactivated autologous serum (AS). After 7 days of culture, the cytokine-induced DCs were pulsed with 20 micrograms/ml of each of the synthesized peptides in the presence of 3 micrograms/ml of beta2-microglobulin for 3 hr at 37 degrees C. in AIM-V Medium. The generated cells appeared to express DC-associated molecules, such as CD80, CD83, CD86 and HLA class II, on their cell surfaces (data not shown). These peptide-pulsed DCs were then inactivated by Mitomycin C (MMC) (30 micrograms/ml for 30 min) and mixed at a 1:20 ratio with autologous CD8+ T cells, obtained by positive selection with CD8 Positive Isolation Kit (Dynal). These cells were set up in 48-well plates (Corning); each well contained $1.5 \times 10^4$ peptide-pulsed DCs, $3 \times 10^5$ CD8+ T cells and 10 ng/ml of IL-7 (R&D System) in 0.5 ml of AIM-V/2% AS medium. Three days later, these cultures were supplemented with IL-2 (CHIRON) to a final concentration of 20 IU/ml. On day 7 and 14, the T cells were further stimulated with the autologous peptide-pulsed DCs. The DCs were prepared each time by the same way described above. CTL was tested against peptide-pulsed A24LCL cells after the 3rd round of peptide stimulation on day 21 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

CTL Expansion Procedure

CTLs were expanded in culture using the method similar to the one described by Riddell et al. (Walter E A et al., N Engl J Med 1995 Oct. 19, 333(16): 1038-44; Riddell S R et al., Nat Med 1996 February, 2(2): 216-23). A total of $5 \times 10^4$ CTLs were suspended in 25 ml of AIM-V/5% AS medium with 2 kinds of human B-lymphoblastoid cell lines, inactivated by MMC, in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS medium containing 30 IU/ml of IL-2 on days 5, 8 and 11 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Establishment of CTL Clones

The dilutions were made to have 0.3, 1, and 3 CTLs/well in 96 round-bottomed micro titer plate (Nalge Nunc International). CTLs were cultured with $1 \times 10^4$ cells/well of 2 kinds of human B-lymphoblastoid cell lines, 30 ng/ml of anti-CD3 antibody, and 125 U/ml of IL-2 in a total of 150 microliters/well of AIM-V Medium containing 5% AS. 50 microliters/well of IL-2 were added to the medium 10 days later so to reach a final concentration of 125 U/ml IL-2. CTL activity was tested on the 14th day, and CTL clones were expanded using the same method as described above (Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Specific CTL Activity

To examine specific CTL activity, interferon (IFN)-gamma enzyme-linked immunospot (ELISPOT) assay and IFN-gamma enzyme-linked immunosorbent assay (ELISA) were performed. Specifically, peptide-pulsed A24LCL ($1 \times 10^4$/well) was prepared as stimulator cells. Cultured Cells in 48 wells or CTL clones after limiting dilution were used as responder cells. IFN-gamma ELISPOT assay and IFN-gamma ELISA assay were performed under manufacture procedure.

Immunogenicity of Epitope Peptides in BALB/c Mice

For priming the peptide-specific CTLs, immunization was given using 100 mlcroliters vaccine mixture, which contains 50 microliters of HLA-A24 restricted peptide and 50 microliters of IFA per mouse. The vaccine was injected s.c. into the right flank of mice for the first immunization on day 0 and in the left flank for the second on the day 7. On day 14, splenocytes from vaccinated mice were used as the responder cells, and RLmale1 cells pulsed with or without peptides were used as the stimulator cells for IFN-gamma ELISPOT assay.

In Vivo Antitumor Effects

Vaccination was done on days −7 and 0 using IFA-conjugated peptide. On day 0, CT26 cells ($5 \times 10^4$ cells per mouse) were injected s.c. into the right flank of BALB/c mice. Tumor growth was measured as the product of two perpendicular diameters ($mm^2$).

Results

Prediction of HLA-A24 Binding Peptides Derived from TEM8

Table 1 shows the HLA-A*2402 and HLA-A*0201 binding peptides of TEM8 in the order of high binding affinity. A total of 21 peptides with potential HLA-A24 binding ability were selected and examined to determine the epitope peptides (Table 1a), and a total of 53 peptides with potential HLA-A2 binding ability were similarly selected and examined to determine the epitope peptides (Table 1b, and Table 1c). Most of the predicted peptides showed no-CTL induction. Therefore, in this invention the peptide which showed CTL induction was focused upon.

TABLE 1a

HLA-A24 binding peptides derived from TEM8 (9mer and 10mer peptides)

| Start Position | Amino acid sequence | Binding score | Positive donor number | Positive well number | Positive CTL line | SEQ ID NO |
|---|---|---|---|---|---|---|
| 446 | WYSPIKGKL | 369.6 | 0/1 | 0/6 | − | 1 |
| 175 | VYCVGVKDF | 100 | 0/1 | 0/6 | − | 2 |
| 39 | CYGGFDLYF | 100 | 1/1 | | | 3 |
| 277 | TYLLCPAPI | 75 | 1/1 | | | 4 |
| 138 | GYRTASVII | 50 | 0/1 | 0/6 | − | 5 |
| 330 | LFLLLALAL | 36 | − | − | − | 6 |
| 84 | VFSTRGTTL | 20 | 0/1 | 0/6 | − | 7 |
| 140 | RTASVIIAL | 11.2 | 0/1 | 0/6 | − | 8 |
| 277 | TYLLCPAPIL | 300 | 1/1 | | | 9 |
| 424 | EYEFPEPRNL | 300 | 0/1 | 0/6 | − | 10 |
| 39 | CYGGFDLYFI | 50 | 0/1 | 0/6 | − | 11 |
| 382 | YYGGRGVGGI | 50 | 0/1 | 0/6 | − | 12 |
| 330 | LFLLLALALL | 30 | − | − | − | 13 |
| 12 | GFQWLSLATL | 30 | 0/1 | 0/6 | − | 14 |
| 64 | YFVEQLAHKF | 23.76 | 0/1 | 0/6 | − | 15 |
| 258 | SFKINDSVTL | 20 | 0/1 | 0/6 | − | 16 |
| 7 | RALGIGFQWL | 17.28 | 0/1 | 0/6 | − | 17 |
| 494 | KYPLNNAYHT | 15 | 0/1 | 0/6 | − | 18 |

TABLE 1a-continued

HLA-A24 binding peptides derived from TEM8 (9mer and 10mer peptides)

| Start Position | Amino acid sequence | Binding score | Positive donor number | Positive well number | Positive CTL line | SEQ ID NO |
|---|---|---|---|---|---|---|
| 445 | KWYSPIKGKL | 12.32 | 0/1 | 0/6 | — | 19 |
| 488 | KNNQPAKYPL | 12 | 0/1 | 0/6 | — | 20 |
| 250 | RNVDRVLCSF | 10.08 | 0/1 | 1/6 | 0/1 | 21 |

TABLE 1b

HLA-A02 binding 9-mer peptides derived from TEM8

| Start Position | Amino acid sequence | Binding score | Positive donor number | Positive well number | Positive CTL line | SEQ ID NO |
|---|---|---|---|---|---|---|
| 266 | TLNEKPFSV | 1653.947 | 0/1 | 0/8 | — | 22 |
| 337 | ALLWWFWPL | 1126.333 | 1/1 | | | 23 |
| 331 | FLLLALALL | 836.253 | — | — | — | 24 |
| 338 | LLWWFWPLC | 452.836 | 1/1 | | | 25 |
| 298 | SMNDGLSFI | 390.792 | 0/1 | 0/8 | — | 26 |
| 8 | ALGIGFQWL | 223.237 | 0/1 | 0/8 | — | 27 |
| 13 | FQWLSLATL | 190.197 | 0/1 | 0/8 | — | 28 |
| 326 | ALLILFLLL | 150.178 | — | — | — | 29 |
| 278 | YLLCPAPIL | 149.071 | 1/1 | | | 30 |
| 47 | FILDKSGSV | 86.756 | 0/1 | 0/8 | — | 31 |
| 327 | LLILFLLLA | 73.815 | — | — | — | 32 |
| 94 | KLTEDREQI | 73.358 | 0/1 | 0/8 | — | 33 |
| 329 | ILFLLLALA | 71.872 | — | — | — | 34 |
| 79 | RMSFIVFST | 71.796 | 0/1 | 0/8 | — | 35 |
| 302 | GLSFISSSV | 69.552 | 0/1 | 0/8 | — | 36 |
| 119 | YMHEGFERA | 63.000 | 0/1 | 0/8 | — | 37 |
| 369 | GLPKKKWPT | 55.890 | 0/1 | 0/8 | — | 38 |
| 453 | KLDALWVLL | 50.843 | 0/1 | 0/8 | — | 39 |
| 112 | VLPGGDTYM | 46.451 | 0/1 | 1/8 | 0/1 | 40 |
| 328 | LILFLLLAL | 42.494 | — | — | — | 41 |
| 15 | WLSLATLVL | 40.289 | 0/1 | 1/8 | 0/1 | 42 |
| 324 | AIALLILFL | 37.157 | — | — | — | 43 |
| 322 | ILAIALLIL | 34.246 | — | — | — | 44 |
| 325 | IALLILFLL | 24.896 | — | — | — | 45 |
| 207 | ALQGIIHSI | 23.995 | 0/1 | 1/8 | 0/1 | 46 |
| 190 | RIADSKDHV | 19.213 | 0/1 | 0/8 | — | 47 |
| 223 | ILAAEPSTI | 17.736 | 0/1 | 0/8 | — | 48 |

TABLE 1b-continued

HLA-A02 binding 9-mer peptides derived from TEM8

| Start Position | Amino acid sequence | Binding score | Positive donor number | Positive well number | Positive CTL line | SEQ ID NO |
|---|---|---|---|---|---|---|
| 104 | QGLEELQKV | 15.841 | 0/1 | 0/8 | — | 49 |
| 170 | DLGAIVYCV | 11.998 | 0/1 | 1/8 | 0/1 | 50 |

TABLE 1c

HLA-A02 binding 10-mer peptides derived from TEM8

| Start Position | Amino acid sequence | Binding score | Positive donor number | Positive well number | Positive CTL line | SEQ ID NO |
|---|---|---|---|---|---|---|
| 459 | VLLRkGYDRV | 321.549 | 0/1 | 0/8 | — | 51 |
| 13 | FQWLsLATLV | 269.238 | 0/1 | 0/8 | — | 52 |
| 326 | ALLIiFLLLA | 160.655 | — | — | — | 53 |
| 329 | ILFLlLALAL | 134.369 | — | — | — | 54 |
| 337 | ALLWwFWPLC | 118.745 | — | — | — | 55 |
| 369 | GLPKkKWPTV | 118.238 | 0/1 | 0/8 | — | 56 |
| 15 | WLSLaTLVLI | 110.379 | 0/1 | 0/8 | — | 57 |
| 47 | FILDkSGSVL | 84.039 | 0/1 | 0/8 | — | 58 |
| 327 | LLILfLLLAL | 83.527 | — | — | — | 59 |
| 338 | LLWWfWPLCC | 70.098 | 1/1 | | | 60 |
| 230 | TICAgESFQV | 55.468 | 0/1 | 0/8 | — | 61 |
| 324 | AIALlILFLL | 39.184 | — | — | — | 62 |
| 265 | VTLNeKPFSV | 35.242 | 1/1 | | | 63 |
| 111 | KVLPgGDTYM | 30.962 | 0/1 | 0/8 | — | 64 |
| 336 | LALLwWFWPL | 26.594 | — | — | — | 65 |
| 103 | RQGLeELQKV | 16.219 | 0/1 | 0/8 | — | 66 |
| 409 | KLEKaKNARV | 15.580 | 0/1 | 0/8 | — | 67 |
| 333 | LLALaLLWWF | 12.019 | 1/1 | | | 68 |
| 83 | IVFStRGTTL | 11.757 | 0/1 | 0/8 | — | 69 |
| 7 | RALGiGFQWL | 11.472 | 0/1 | 0/8 | — | 70 |
| 17 | SLATlVLICA | 11.426 | — | — | — | 71 |
| 305 | FISSsVIITT | 10.841 | — | — | — | 72 |
| 294 | ALQVsMNDGL | 10.468 | 0/1 | 0/8 | — | 73 |
| 321 | SILAiALLIL | 10.249 | — | — | — | 74 |

Start position indicates the number of amino acid residue from the N-terminus of TEM8.
Binding score is derived from "BIMAS".

CTL Induction with the Predicted Peptides from TEM8 Restricted with HLA-A*2402 or HLA-A*0201 and Establishment for CTL Lines Stimulated with TEM8 Derived Peptides CTLs for those peptides derived from TEM8 were generated according to the protocols as described in "Materials and Methods". Peptide specific CTL activity was determined by IFN-gamma ELISPOT assay (FIG. 1a-i). It showed that TEM8-A24-9-39 (SEQ ID NO: 3), TEM8-A24-9-277 (SEQ ID NO: 4), TEM8-A24-10-277 (SEQ ID NO: 9), TEM8-A02-9-337 (SEQ ID NO: 23), TEM8-A02-9-338 (SEQ ID NO: 25), TEM8-A02-9-278 (SEQ ID NO: 30), TEM8-A02-10-338 (SEQ ID NO: 60), TEM8-A02-10-265 (SEQ ID NO: 63) and TEM8-A02-10-333 (SEQ ID NO: 68) demonstrated potent IFN-gamma production as compared to the control wells. Furthermore, the cells in the positive well number #5 stimulated with SEQ ID NO: 3, #6 with SEQ ID NO: 4, #3 with SEQ ID NO: 9, #3 with SEQ ID NO: 23, #6 with SEQ ID NO: 25, #3 with SEQ ID NO: 30, #2 with SEQ ID NO: 60, #5 with SEQ ID NO: 63 and #4 with SEQ ID NO: 68 were expanded and established CTL lines. CTL activity of those CTL lines was determined by IFN-gamma ELISA assay (FIG. 2a-i). It showed that all CTL lines demonstrated potent IFN-gamma production against the target cells pulsed with corresponding peptide as compared to target cells without peptide pulse. On the other hand, no CTL lines could be established by stimulation with other peptides shown in Table 1, despite those peptide had possible binding activity with HLA-A*2402 or HLA-A*0201. For example, typical negative data of CTL response stimulated with TEM8-A02-9-207 (SEQ ID NO: 46) was shown in FIG. 1j and FIG. 2j. As a result, it indicated that nine peptides derived from TEM8 were screened as the peptides could induce potent CTL lines.

Establishment of CTL Clones Against TEM8 Specific Peptides

Figure 3:
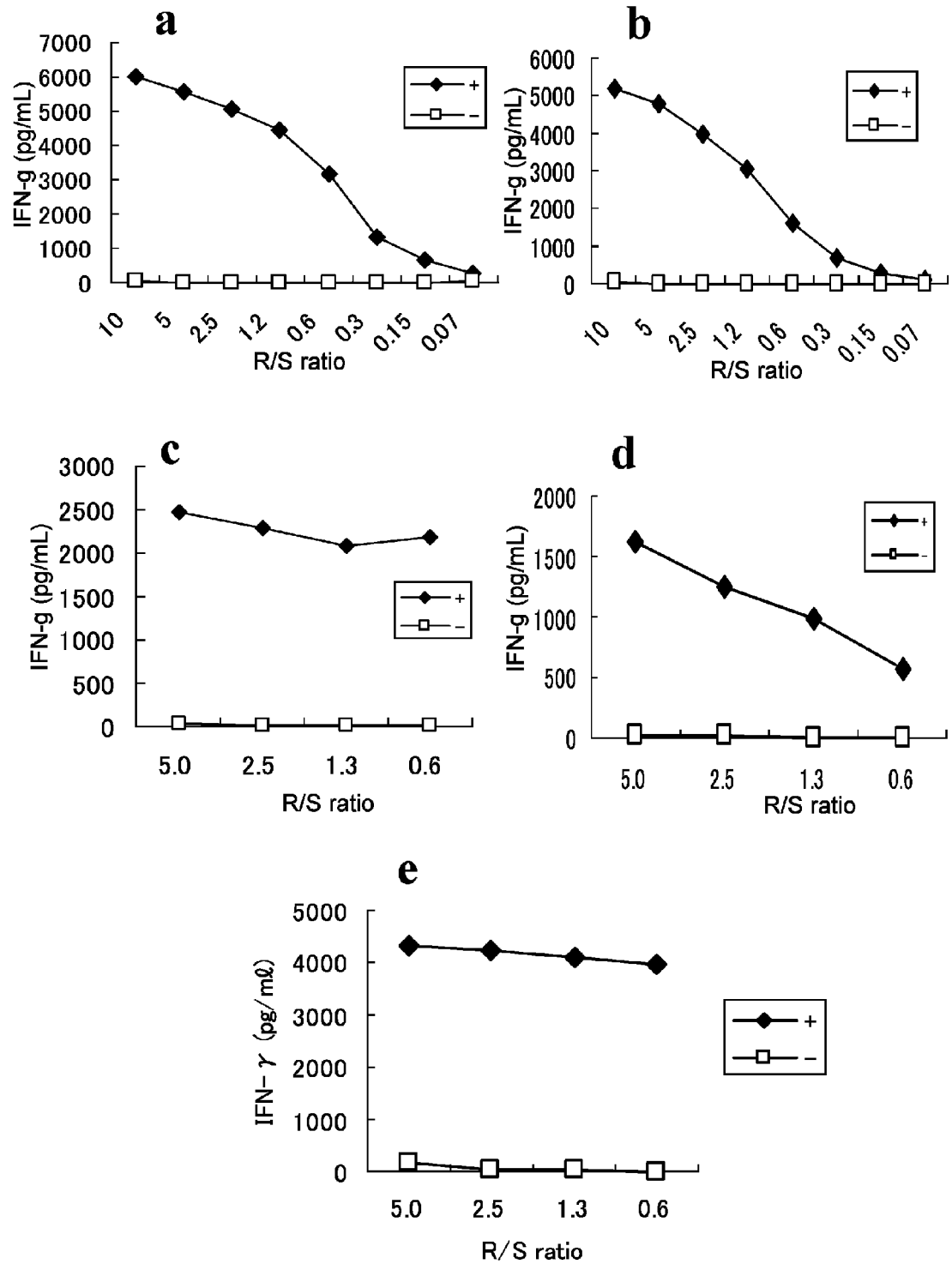
FIG. 3 depicts line graphs showing the establishment of CTL clones stimulated with TEM8-A24-9-277 (SEQ ID NO:4) (a) TEM8-A24-10-277 (SEQ ID NO:9) (b), TEM8-A02-9-337 (SEQ ID NO: 23) (c), TEM8-A02-9-338 (SEQ ID NO: 25) (d) and TEM8-A02-10-265 (SEQ ID NO: 63) (e). CTL clones established by stimulation with each peptide demonstrated potent IFN-gamma production against target cells pulsed corresponding peptide. On the other hand, no IFN-gamma production was shown against target cells not pulsed with any peptides. In the figures, "+" indicated the IFN-gamma production against target cells pulsed with the appropriate peptide, and "−" indicated the IFN-gamma production against target cells not pulsed with any peptides.

Furthermore, CTL clones were established by limiting dilution from each CTL lines as described in under the item of "Materials and Methods", and IFN-gamma production from CTL clones against target cells pulsed peptide were determined by IFN-gamma ELISA assay. Potent IFN-gamma production were determined from CTL clones stimulated with SEQ ID NO: 4, SEQ ID NO: 9, SEQ ID NO: 23, SEQ ID NO: 25 and SEQ ID NO: 63 in FIG. 3.

Specific CTL Activity Against Target Cells Endogenously Expressing TEM8 and HLA-A*2402 or HLA-A*0201

Figure 4:
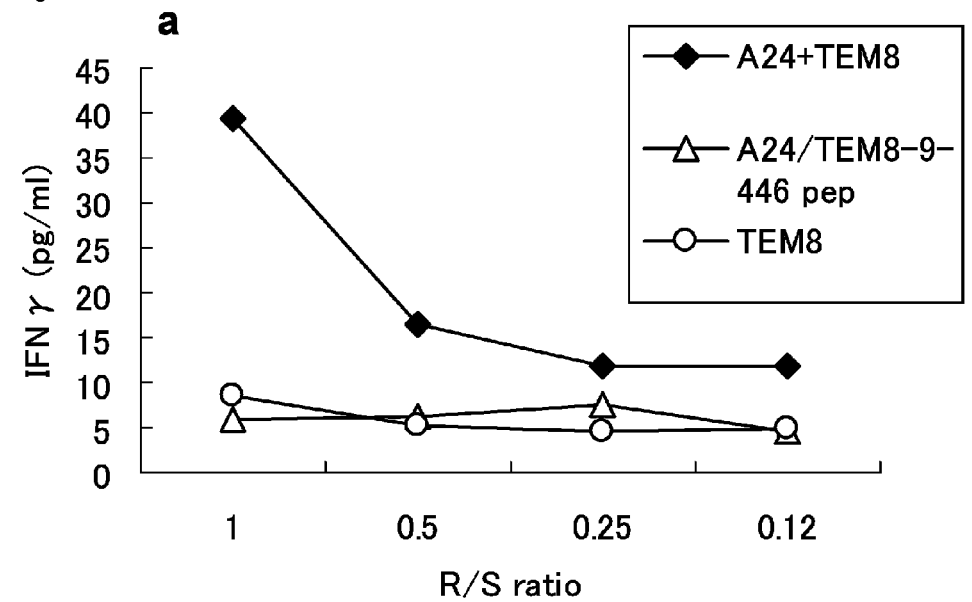
FIG. 4 depicts line graphs showing specific CTL activity against the target cells that endogenously express TEM8 and HLA-A*2402 or HLA-A*0201. COS7 cells transfected with the full length TEM8 gene or with corresponding HLA gene pulsing with inappropriate peptide derived from TEM8 were prepared as control. (a) The CTL clone established with TEM8-A24-9-277 (SEQ ID NO: 4) showed high specific CTL activity against COS7 cells transfected with both TEM8 and HLA-A24 (black lozenge-mark). On the other hand, no significant specific CTL activity was detected against target cells expressing either HLA-A*2402 (open triangular mark) or TEM8 (open circle). (b) The CTL clone established with TEM8-A02-10-265 (SEQ ID NO: 63) showed high specific CTL activity against COS7 cells transfected with both TEM8 and HLA-A02 (black lozenge-mark). On the other hand, no significant specific CTL activity was detected against target cells expressing either HLA-A*0201 (open triangular mark) or TEM8 (open circle).
Figure 4:
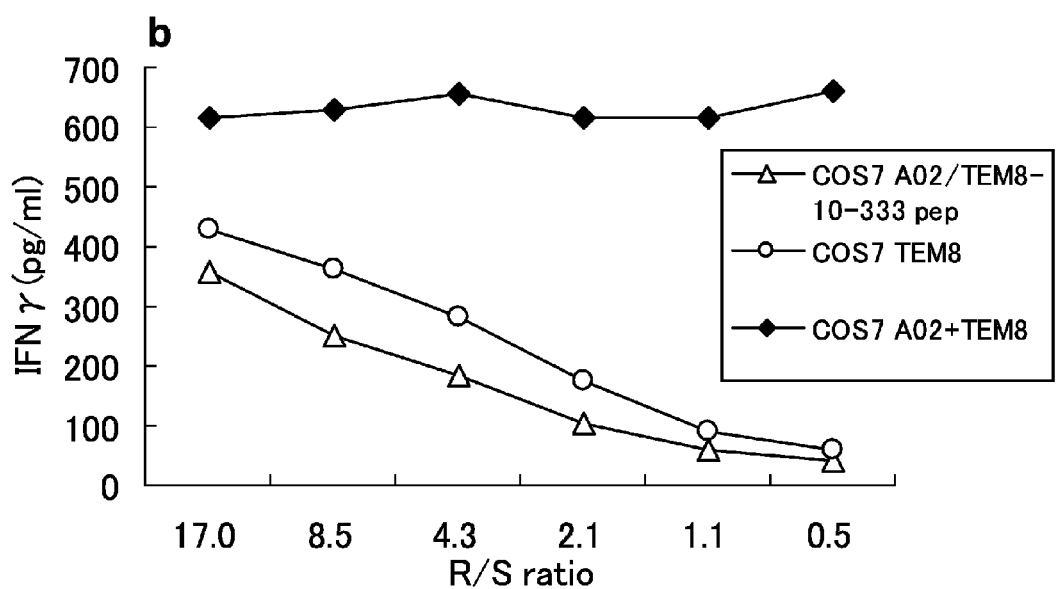

The established CTL lines or clones raised against these peptides were examined for their ability to recognize target cells that endogenously express TEM8 and HLAA*2402 molecule. Specific CTL activity against COS7 cells which were transfected with both the full length of TEM8 and HLA-A*2402 molecule genes (a specific model for the target cells that endogenously express TEM8 and HLA-A*2402 genes) was tested using the CTL lines or clones raised by corresponding peptide as the effector cells. COS7 cells transfected with either the full length of TEM8 genes or HLA-A* 2402, were prepared as control. The CTLs showed potent CTL activity against COS7 cells transfected with both TEM8 and HLA-A24 in FIG. 4a. On the other hand, no significant specific CTL activity was detected against the controls. Furthermore, established CTL lines or clones raised against HLA-A2 restricted peptides were also examined for their ability to recognize target cells that endogenously express TEM8 and HLA-A*0201 molecule. Specific CTL activity against COS7 cells which were transfected with both the full length of TEM8 and HLA-A*0201 molecule genes was tested. The CTL lines or clones induced by corresponding HLA-A2 restricted peptide were used as the effector cells. COS7 cells transfected with either full length of TEM8 gene or HLA-A*0201 gene were used as control. The CTLs stimulated with SEQ ID NO: 63 showed potent CTL activity against COS7 cells transfected with both TEM8 and HLA-A2 in FIG. 4b. On the other hand, no significant specific CTL activity was detected against the controls. Thus, these data clearly demonstrated that SEQ ID NO: 4 and SEQ ID NO: 63 were naturally expressed on the target cells with HLA-A*2402 or HLA-A*0201 molecule and were recognized by the CTLs. Furthermore, it indicated that those two peptides derived from TEM8 are epitope peptides could induce CTLs and it may be available to apply the cancer vaccines for patients with TEM8 expressing cells.

Immunogenicity of Epitope Peptide in BALB/c Mice

Immunization of SEQ ID NO: 4 to BALB/c mice was performed to evaluate the immunogenicity of TEM8 epitope peptides After second injection of the peptide conjugated with IFA, peptide specific CTL activity was determined by IFN-gamma ELISPOT assay. When the splenocytes harvested from the vaccinated mice were used as responder cells, potent IFN-gamma production was specifically detected In FIG. 5a, IFN-gamma production specific to SEQ ID NO: 4 were detected from four of five mice (M1, M3, M4 and M5) but not in control mice (N1 and N2). These data indicated that SEQ ID NO: 4 induced specific CTLs against peptide-pulsed target cells in vivo.

Antitumor Effects of Vaccination of TEM8 Epitope Peptide

To examine the antitumor effects using the peptide, in vivo anti-tumor model was examined using CT26 tumor cell lines. Administration of SEQ ID NO: 4 was performed on the day −7 and 0, and CT26 colorectal cancer cells were injected s.c. into BALB/c mice on day 0. Tumor growth apparently reduced in the mice vaccinated of SEQ ID NO: 4 compared with the control mice (FIG. 5b). It showed the statistically significant difference with suppression of tumor growth in the mice with vaccination using SEQ ID NO: 4 ($P<0.05$).

Homology Analysis of Antigen Peptides

It was demonstrated that the CTLs stimulated with the following peptides respectively, showed significant and specific CTL activity.

TEM8-A24-9-39 (SEQ ID NO: 3),
TEM8-A24-9-277 (SEQ ID NO: 4),
TEM8-A24-10-277 (SEQ ID NO: 9),
TEM8-A02-9-337 (SEQ ID NO: 23),
TEM8-A02-9-338 (SEQ ID NO: 25),
TEM8-A02-9-278 (SEQ ID NO: 30),
TEM8-A02-10-338 (SEQ ID NO: 60),
TEM8-A02-10-265 (SEQ ID NO: 63) and
TEM8-A02-10-333 (SEQ ID NO: 68), This result may be due to the fact that the sequences of the peptides are homologous to peptides derived from other molecules that are known to sensitize the human immune system. To exclude this possibility, homology analysis was performed for these peptide sequences using as queries the BLAST algorithm (http://www.ncbi.nlm.nih.gov/blast/blast.cgi) which revealed no sequence with significant homology. The results of homology analyses indicate that the sequences of TEM8-A24-9-39 (SEQ ID NO: 3), TEM8-A24-9-277 (SEQ ID NO: 4), TEM8-A24-10-277 (SEQ ID NO: 9), TEM8-A02-9-337 (SEQ ID NO: 23), TEM8-A02-9-338 (SEQ ID NO: 25), TEM8-A02-9-278 (SEQ ID NO: 30), TEM8-A02-10-338 (SEQ ID NO: 60), TEM8-A02-10-265 (SEQ ID NO: 63) and TEM8-A02-10-333 (SEQ ID NO: 68), respectively, are unique and thus, there is little possibility, to our best knowledge, that these molecules raise an unintended immunologic response to some unrelated molecule.

Finally, novel HLA-A*2402 or A*0201 epitope peptides derived from TEM8 were identified. Furthermore, it was demonstrated that epitope peptides of TEM8 are applicable for cancer immunotherapy.

INDUSTRIAL APPLICABILITY

The present invention provides novel peptides, which induce CTLs targeting endothelial cells formed in a wide range of diseases associated with angiogenesis, and which peptides are extremely effective as vaccines. The present invention also provides pharmaceuticals for treating and prevention of diseases associated with angiogenesis, such as tumors, which comprise any of these peptides as the active ingredient. According to the present invention, the size of the peptide required for inducing immunity is very small (e.g., 9 to 10 amino acid residues). Therefore, the present invention is particularly advantageous in that the synthesis and purification of the peptides can be quite easily performed.

All publications, patents, and patent applications cited herein are incorporated into the present description by reference.

The invention claimed is:

1. An isolated nonapeptide or decapeptide having cytotoxic T cell inducibility, wherein said nonapeptide or decapeptide comprises an amino acid sequence selected from the amino acid sequence of SEQ ID NO: 76.

2. A nonapeptide or decapeptide comprising the amino acid sequence selected from the group consisting of SEQ ID NOs: 3, 4 and 9.

3. A peptide of less than 15 amino acids having cytotoxic T lymphocyte (CTL) inducibility, wherein the peptide comprises the amino acid sequence selected from the group of:
   (a) SEQ ID NO: 3, 4 or 9; and
   (b) SEQ ID NO: 3, 4 or 9 in which 1 or 2 amino acids are substituted or added.

4. The peptide of claim 3 having at least one substitution selected from the group consisting of:
   (a) the second amino acid from the N-terminus of the amino acid sequence of SEQ ID NOs: 3, 4 or 9 is selected from the group of phenylalanine, tyrosine, methionine and tryptophan, and
   (b) the C-terminal amino acid of the amino acid sequence of SEQ ID NOs: 3, 4 or 9 is selected from the group of phenylalanine, leucine, isoleucine, tryptophan and methionine.

5. A nonapeptide or decapeptide comprising the amino acid sequence selected from the group consisting of SEQ ID NO: 23, 25, 30, 60, 63 and 68.

6. A peptide of less than 15 amino acids having CTL inducibility, wherein the peptide comprises the amino acid sequence selected from the group of:
   (a) SEQ ID NO: 23, 25, 30, 60, 63 or 68; and
   (b) SEQ ID NO: 23, 25, 30, 60, 63 or 68 in which 1 or 2 amino acids are substituted or added.

7. The peptide of claim 6 having at least one substitution selected from the group consisting of:
   (a) the second amino acid from the N-terminus of the amino acid sequence of SEQ ID NO: 23, 25, 30, 60, 63 or 68 is leucine or methionine, and
   (b) the C-terminal amino acid of the amino acid sequence of SEQ ID NO: 23, 25, 30, 60, 63 or 68 is valine or leucine.

8. A method for inducing an antigen-presenting cell with high CTL inducibility by using one of the following peptides:
   (a) an isolated nonapeptide or decapeptide having cytotoxic T cell inducibility, wherein said nonapeptide or decapeptide comprises an amino acid sequence selected from the amino acid sequence of SEQ ID NO: 76;
   (b) a nonapeptide or decapeptide comprising the amino acid sequence selected from the group consisting of SEQ ID NOs: 3, 4 and 9;
   (c) a peptide of less than 15 amino acids having cytotoxic T lymphocyte (CTL) inducibility, wherein the peptide comprises the amino acid sequence selected from the group of SEQ ID NO: 3, 4 or 9; and SEQ ID NO: 3, 4 or 9 in which 1 or 2 amino acids are substituted or added;
   (d) a nonapeptide or decapeptide comprising of the amino acid sequence selected from the group consisting of SEQ ID NO: 23, 25, 30, 60, 63 and 68, or;
   (e) a peptide of less than 15 amino acids having cytotoxic T lymphocyte (CTL) inducibility, wherein the peptide comprises the amino acid sequence selected from the group consisting of SEQ ID NO: 23, 25, 30, 60, 63 or 68, and SEQ ID NO: 23, 25, 30, 60, 63 or 68, in which 1 or 2 amino acids are substituted or added.

9. A method for inducing CTL by using a peptide of any one of the following peptides:
   (a) an isolated nonapeptide or decapeptide having cytotoxic T cell inducibility, wherein said nonapeptide or decapeptide comprises an amino acid sequence selected from the amino acid sequence of SEQ ID NO: 76;

(b) a nonapeptide or decapeptide comprising the amino acid sequence selected from the group consisting of SEQ ID NOs: 3, 4 and 9;

(c) a peptide of less than 15 amino acids having cytotoxic T lymphocyte (CTL) inducibility, wherein the peptide comprises the amino acid sequence selected from the group of SEQ ID NO: 3, 4 or 9; and SEQ ID NO: 3, 4 or 9 in which 1 or 2 amino acids are substituted or added;

(d) a nonapeptide or decapeptide comprising of the amino acid sequence selected from the group consisting of SEQ ID NO: 23, 25, 30, 60, 63 and 68, or;

(e) a peptide of less than 15 amino acids having cytotoxic T lymphocyte (CTL) inducibility, wherein the peptide comprises the amino acid sequence selected from the group consisting of SEQ ID NO: 23, 25, 30, 60, 63 or 68, and SEQ ID NO: 23, 25, 30, 60, 63 or 68, in which 1 or 2 amino acids are substituted or added.

* * * * *

UNITED STATES PATENT AND TRADEMARK OFFICE
CERTIFICATE OF CORRECTION

PATENT NO. : 8,367,799 B2
APPLICATION NO. : 12/595197
DATED : February 5, 2013
INVENTOR(S) : Tsunoda et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 596 days.

Signed and Sealed this

First Day of September, 2015

Michelle K. Lee
*Director of the United States Patent and Trademark Office*

SEQUENCE LISTING

```
<160> NUMBER OF SEQ ID NOS: 76

<210> SEQ ID NO 1
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 1

Trp Tyr Ser Pro Ile Lys Gly Lys Leu
1               5

<210> SEQ ID NO 2
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 2

Val Tyr Cys Val Gly Val Lys Asp Phe
1               5

<210> SEQ ID NO 3
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 3

Cys Tyr Gly Gly Phe Asp Leu Tyr Phe
1               5

<210> SEQ ID NO 4
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 4

Thr Tyr Leu Leu Cys Pro Ala Pro Ile
1               5

<210> SEQ ID NO 5
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 5

Gly Tyr Arg Thr Ala Ser Val Ile Ile
1               5
```

```
<210> SEQ ID NO 6
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 6

Leu Phe Leu Leu Leu Ala Leu Ala Leu
1               5

<210> SEQ ID NO 7
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 7

Val Phe Ser Thr Arg Gly Thr Thr Leu
1               5

<210> SEQ ID NO 8
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 8

Arg Thr Ala Ser Val Ile Ile Ala Leu
1               5

<210> SEQ ID NO 9
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 9

Thr Tyr Leu Leu Cys Pro Ala Pro Ile Leu
1               5                   10

<210> SEQ ID NO 10
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 10

Glu Tyr Glu Phe Pro Glu Pro Arg Asn Leu
1               5                   10

<210> SEQ ID NO 11
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 11

Cys Tyr Gly Gly Phe Asp Leu Tyr Phe Ile
1               5                   10
```

```
<210> SEQ ID NO 12
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 12

Tyr Tyr Gly Gly Arg Gly Val Gly Gly Ile
1               5                   10

<210> SEQ ID NO 13
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 13

Leu Phe Leu Leu Leu Ala Leu Ala Leu Leu
1               5                   10

<210> SEQ ID NO 14
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 14

Gly Phe Gln Trp Leu Ser Leu Ala Thr Leu
1               5                   10

<210> SEQ ID NO 15
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 15

Tyr Phe Val Glu Gln Leu Ala His Lys Phe
1               5                   10

<210> SEQ ID NO 16
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 16

Ser Phe Lys Ile Asn Asp Ser Val Thr Leu
1               5                   10

<210> SEQ ID NO 17
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 17

Arg Ala Leu Gly Ile Gly Phe Gln Trp Leu
1               5                   10
```

```
<210> SEQ ID NO 18
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 18

Lys Tyr Pro Leu Asn Asn Ala Tyr His Thr
1               5                   10

<210> SEQ ID NO 19
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 19

Lys Trp Tyr Ser Pro Ile Lys Gly Lys Leu
1               5                   10

<210> SEQ ID NO 20
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 20

Lys Asn Asn Gln Pro Ala Lys Tyr Pro Leu
1               5                   10

<210> SEQ ID NO 21
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 21

Arg Asn Val Asp Arg Val Leu Cys Ser Phe
1               5                   10

<210> SEQ ID NO 22
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 22

Thr Leu Asn Glu Lys Pro Phe Ser Val
1               5

<210> SEQ ID NO 23
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 23

Ala Leu Leu Trp Trp Phe Trp Pro Leu
1               5
```

-continued

```
<210> SEQ ID NO 24
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 24

Phe Leu Leu Leu Ala Leu Ala Leu Leu
1               5

<210> SEQ ID NO 25
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 25

Leu Leu Trp Trp Phe Trp Pro Leu Cys
1               5

<210> SEQ ID NO 26
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 26

Ser Met Asn Asp Gly Leu Ser Phe Ile
1               5

<210> SEQ ID NO 27
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 27

Ala Leu Gly Ile Gly Phe Gln Trp Leu
1               5

<210> SEQ ID NO 28
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 28

Phe Gln Trp Leu Ser Leu Ala Thr Leu
1               5

<210> SEQ ID NO 29
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 29

Ala Leu Leu Ile Leu Phe Leu Leu Leu
1               5
```

-continued

```
<210> SEQ ID NO 30
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 30

Tyr Leu Leu Cys Pro Ala Pro Ile Leu
1               5

<210> SEQ ID NO 31
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 31

Phe Ile Leu Asp Lys Ser Gly Ser Val
1               5

<210> SEQ ID NO 32
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 32

Leu Leu Ile Leu Phe Leu Leu Leu Ala
1               5

<210> SEQ ID NO 33
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 33

Lys Leu Thr Glu Asp Arg Glu Gln Ile
1               5

<210> SEQ ID NO 34
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 34

Ile Leu Phe Leu Leu Leu Ala Leu Ala
1               5

<210> SEQ ID NO 35
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 35

Arg Met Ser Phe Ile Val Phe Ser Thr
1               5
```

-continued

```
<210> SEQ ID NO 36
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 36

Gly Leu Ser Phe Ile Ser Ser Ser Val
1               5

<210> SEQ ID NO 37
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 37

Tyr Met His Glu Gly Phe Glu Arg Ala
1               5

<210> SEQ ID NO 38
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 38

Gly Leu Pro Lys Lys Lys Trp Pro Thr
1               5

<210> SEQ ID NO 39
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 39

Lys Leu Asp Ala Leu Trp Val Leu Leu
1               5

<210> SEQ ID NO 40
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 40

Val Leu Pro Gly Gly Asp Thr Tyr Met
1               5

<210> SEQ ID NO 41
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 41

Leu Ile Leu Phe Leu Leu Leu Ala Leu
1               5
```

```
<210> SEQ ID NO 42
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 42

Trp Leu Ser Leu Ala Thr Leu Val Leu
1               5

<210> SEQ ID NO 43
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 43

Ala Ile Ala Leu Leu Ile Leu Phe Leu
1               5

<210> SEQ ID NO 44
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 44

Ile Leu Ala Ile Ala Leu Leu Ile Leu
1               5

<210> SEQ ID NO 45
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 45

Ile Ala Leu Leu Ile Leu Phe Leu Leu
1               5

<210> SEQ ID NO 46
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 46

Ala Leu Gln Gly Ile Ile His Ser Ile
1               5

<210> SEQ ID NO 47
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 47

Arg Ile Ala Asp Ser Lys Asp His Val
1               5
```

```
<210> SEQ ID NO 48
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 48

Ile Leu Ala Ala Glu Pro Ser Thr Ile
1               5

<210> SEQ ID NO 49
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 49

Gln Gly Leu Glu Glu Leu Gln Lys Val
1               5

<210> SEQ ID NO 50
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 50

Asp Leu Gly Ala Ile Val Tyr Cys Val
1               5

<210> SEQ ID NO 51
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 51

Val Leu Leu Arg Lys Gly Tyr Asp Arg Val
1               5                   10

<210> SEQ ID NO 52
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 52

Phe Gln Trp Leu Ser Leu Ala Thr Leu Val
1               5                   10

<210> SEQ ID NO 53
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 53

Ala Leu Leu Ile Leu Phe Leu Leu Leu Ala
1               5                   10
```

```
<210> SEQ ID NO 54
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 54

Ile Leu Phe Leu Leu Leu Ala Leu Ala Leu
1               5                   10

<210> SEQ ID NO 55
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 55

Ala Leu Leu Trp Trp Phe Trp Pro Leu Cys
1               5                   10

<210> SEQ ID NO 56
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 56

Gly Leu Pro Lys Lys Lys Trp Pro Thr Val
1               5                   10

<210> SEQ ID NO 57
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 57

Trp Leu Ser Leu Ala Thr Leu Val Leu Ile
1               5                   10

<210> SEQ ID NO 58
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 58

Phe Ile Leu Asp Lys Ser Gly Ser Val Leu
1               5                   10

<210> SEQ ID NO 59
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 59

Leu Leu Ile Leu Phe Leu Leu Leu Ala Leu
1               5                   10
```

```
<210> SEQ ID NO 60
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 60

Leu Leu Trp Trp Phe Trp Pro Leu Cys Cys
1               5                   10

<210> SEQ ID NO 61
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 61

Thr Ile Cys Ala Gly Glu Ser Phe Gln Val
1               5                   10

<210> SEQ ID NO 62
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 62

Ala Ile Ala Leu Leu Ile Leu Phe Leu Leu
1               5                   10

<210> SEQ ID NO 63
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 63

Val Thr Leu Asn Glu Lys Pro Phe Ser Val
1               5                   10

<210> SEQ ID NO 64
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 64

Lys Val Leu Pro Gly Gly Asp Thr Tyr Met
1               5                   10

<210> SEQ ID NO 65
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 65

Leu Ala Leu Leu Trp Trp Phe Trp Pro Leu
1               5                   10
```

-continued

```
<210> SEQ ID NO 66
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 66

Arg Gln Gly Leu Glu Glu Leu Gln Lys Val
1               5                   10

<210> SEQ ID NO 67
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 67

Lys Leu Glu Lys Ala Lys Asn Ala Arg Val
1               5                   10

<210> SEQ ID NO 68
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 68

Leu Leu Ala Leu Ala Leu Leu Trp Trp Phe
1               5                   10

<210> SEQ ID NO 69
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 69

Ile Val Phe Ser Thr Arg Gly Thr Thr Leu
1               5                   10

<210> SEQ ID NO 70
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 70

Arg Ala Leu Gly Ile Gly Phe Gln Trp Leu
1               5                   10

<210> SEQ ID NO 71
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 71

Ser Leu Ala Thr Leu Val Leu Ile Cys Ala
1               5                   10
```

```
<210> SEQ ID NO 72
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 72

Phe Ile Ser Ser Ser Val Ile Ile Thr Thr
1               5                   10

<210> SEQ ID NO 73
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 73

Ala Leu Gln Val Ser Met Asn Asp Gly Leu
1               5                   10

<210> SEQ ID NO 74
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 74

Ser Ile Leu Ala Ile Ala Leu Leu Ile Leu
1               5                   10

<210> SEQ ID NO 75
<211> LENGTH: 5540
<212> TYPE: DNA
<213> ORGANISM: Homo sapiens
<220> FEATURE:
<221> NAME/KEY: CDS
<222> LOCATION: (144)..(1835)

<400> SEQUENCE: 75
aattgcttcc ggggagttgc gagggagcga gggggaataa aggacccgcg aggaagggcc      60
cgcggatggc gcgtccctga gggtcgtggc gagttcgcgg agcgtgggaa ggagcggacc     120
ctgctctccc cgggctgcgg gcc atg gcc acg gcg gag cgg aga gcc ctc ggc     173
                        Met Ala Thr Ala Glu Arg Arg Ala Leu Gly
                        1               5                   10 atc ggc ttc cag tgg ctc tct ttg gcc act ctg gtg ctc atc tgc gcc       221
Ile Gly Phe Gln Trp Leu Ser Leu Ala Thr Leu Val Leu Ile Cys Ala
                15                  20                  25 ggg caa ggg gga cgc agg gag gat ggg ggt cca gcc tgc tac ggc gga       269
Gly Gln Gly Gly Arg Arg Glu Asp Gly Gly Pro Ala Cys Tyr Gly Gly
        30                  35                  40 ttt gac ctg tac ttc att ttg gac aaa tca gga agt gtg ctg cac cac       317
Phe Asp Leu Tyr Phe Ile Leu Asp Lys Ser Gly Ser Val Leu His His
    45                  50                  55 tgg aat gaa atc tat tac ttt gtg gaa cag ttg gct cac aaa ttc atc       365
Trp Asn Glu Ile Tyr Tyr Phe Val Glu Gln Leu Ala His Lys Phe Ile
60                  65                  70 agc cca cag ttg aga atg tcc ttt att gtt ttc tcc acc cga gga aca       413
Ser Pro Gln Leu Arg Met Ser Phe Ile Val Phe Ser Thr Arg Gly Thr
75                  80                  85                  90 acc tta atg aaa ctg aca gaa gac aga gaa caa atc cgt caa ggc cta       461
Thr Leu Met Lys Leu Thr Glu Asp Arg Glu Gln Ile Arg Gln Gly Leu
                95                  100                 105
```

| | | |
|---|---|---|
| gaa gaa ctc cag aaa gtt ctg cca gga gga gac act tac atg cat gaa<br>Glu Glu Leu Gln Lys Val Leu Pro Gly Gly Asp Thr Tyr Met His Glu<br>110                       115                     120 | | 509 |
| gga ttt gaa agg gcc agt gag cag att tat tat gaa aac aga caa ggg<br>Gly Phe Glu Arg Ala Ser Glu Gln Ile Tyr Tyr Glu Asn Arg Gln Gly<br>          125                     130                     135 | | 557 |
| tac agg aca gcc agc gtc atc att gct ttg act gat gga gaa ctc cat<br>Tyr Arg Thr Ala Ser Val Ile Ile Ala Leu Thr Asp Gly Glu Leu His<br>140                       145                     150 | | 605 |
| gaa gat ctc ttt ttc tat tca gag agg gag gct aat agg tct cga gat<br>Glu Asp Leu Phe Phe Tyr Ser Glu Arg Glu Ala Asn Arg Ser Arg Asp<br>155                       160                     165                     170 | | 653 |
| ctt ggt gca att gtt tac tgt gtt ggt gtg aaa gat ttc aat gag aca<br>Leu Gly Ala Ile Val Tyr Cys Val Gly Val Lys Asp Phe Asn Glu Thr<br>                    175                     180                     185 | | 701 |
| cag ctg gcc cgg att gcg gac agt aag gat cat gtg ttt ccc gtg aat<br>Gln Leu Ala Arg Ile Ala Asp Ser Lys Asp His Val Phe Pro Val Asn<br>                  190                     195                     200 | | 749 |
| gac ggc ttt cag gct ctg caa ggc atc atc cac tca att ttg aag aag<br>Asp Gly Phe Gln Ala Leu Gln Gly Ile Ile His Ser Ile Leu Lys Lys<br>          205                     210                     215 | | 797 |
| tcc tgc atc gaa att cta gca gct gaa cca tcc acc ata tgt gca gga<br>Ser Cys Ile Glu Ile Leu Ala Ala Glu Pro Ser Thr Ile Cys Ala Gly<br>220                       225                     230 | | 845 |
| gag tca ttt caa gtt gtc gtg aga gga aac ggc ttc cga cat gcc cgc<br>Glu Ser Phe Gln Val Val Val Arg Gly Asn Gly Phe Arg His Ala Arg<br>235                       240                     245                     250 | | 893 |
| aac gtg gac agg gtc ctc tgc agc ttc aag atc aat gac tcg gtc aca<br>Asn Val Asp Arg Val Leu Cys Ser Phe Lys Ile Asn Asp Ser Val Thr<br>                  255                     260                     265 | | 941 |
| ctc aat gag aag ccc ttt tct gtg gaa gat act tat tta ctg tgt cca<br>Leu Asn Glu Lys Pro Phe Ser Val Glu Asp Thr Tyr Leu Leu Cys Pro<br>          270                     275                     280 | | 989 |
| gcg cct atc tta aaa gaa gtt ggc atg aaa gct gca ctc cag gtc agc<br>Ala Pro Ile Leu Lys Glu Val Gly Met Lys Ala Ala Leu Gln Val Ser<br>                  285                     290                     295 | | 1037 |
| atg aac gat ggc ctc tct ttt atc tcc agt tct gtc atc atc acc acc<br>Met Asn Asp Gly Leu Ser Phe Ile Ser Ser Ser Val Ile Ile Thr Thr<br>300                       305                     310 | | 1085 |
| aca cac tgt tct gac ggt tcc atc ctg gcc atc gcc ctg ctg atc ctg<br>Thr His Cys Ser Asp Gly Ser Ile Leu Ala Ile Ala Leu Leu Ile Leu<br>315                       320                     325                     330 | | 1133 |
| ttc ctg ctc cta gcc ctg gct ctc ctc tgg tgg ttc tgg ccc ctc tgc<br>Phe Leu Leu Leu Ala Leu Ala Leu Leu Trp Trp Phe Trp Pro Leu Cys<br>                  335                     340                     345 | | 1181 |
| tgc act gtg att atc aag gag gtc cct cca ccc cct gcc gag gag agt<br>Cys Thr Val Ile Ile Lys Glu Val Pro Pro Pro Pro Ala Glu Glu Ser<br>          350                     355                     360 | | 1229 |
| gag gaa gaa gat gat gat ggt ctg cct aag aaa aag tgg cca acg gta<br>Glu Glu Glu Asp Asp Asp Gly Leu Pro Lys Lys Lys Trp Pro Thr Val<br>365                       370                     375 | | 1277 |
| gac gcc tct tat tat ggt ggg aga ggc gtt gga ggc att aaa aga atg<br>Asp Ala Ser Tyr Tyr Gly Gly Arg Gly Val Gly Gly Ile Lys Arg Met<br>380                       385                     390 | | 1325 |
| gag gtt cgt tgg gga gaa aag ggc tcc aca gaa gaa ggt gct aag ttg<br>Glu Val Arg Trp Gly Glu Lys Gly Ser Thr Glu Glu Gly Ala Lys Leu<br>395                       400                     405                     410 | | 1373 |
| gaa aag gca aag aat gca aga gtc aag atg ccg gag cag gaa tat gaa<br>Glu Lys Ala Lys Asn Ala Arg Val Lys Met Pro Glu Gln Glu Tyr Glu<br>                  415                     420                     425 | | 1421 |

```
ttc cct gag ccg cga aat ctc aac aac aat atg cgt cgg cct tct tcc      1469
Phe Pro Glu Pro Arg Asn Leu Asn Asn Asn Met Arg Arg Pro Ser Ser
            430                 435                 440 ccc cgg aag tgg tac tct cca atc aag gga aaa ctc gat gcc ttg tgg      1517
Pro Arg Lys Trp Tyr Ser Pro Ile Lys Gly Lys Leu Asp Ala Leu Trp
            445                 450                 455 gtc cta ctg agg aaa gga tat gat cgt gtg tct gtg atg cgt cca cag      1565
Val Leu Leu Arg Lys Gly Tyr Asp Arg Val Ser Val Met Arg Pro Gln
        460                 465                 470 cca gga gac acg ggg cgc tgc atc aac ttc acc agg gtc aag aac aac      1613
Pro Gly Asp Thr Gly Arg Cys Ile Asn Phe Thr Arg Val Lys Asn Asn
475                 480                 485                 490 cag cca gcc aag tac cca ctc aac aac gcc tac cac acc tcc tcg ccg      1661
Gln Pro Ala Lys Tyr Pro Leu Asn Asn Ala Tyr His Thr Ser Ser Pro
                495                 500                 505 cct cct gcc ccc atc tac act ccc cca cct cct gcg ccc cac tgc cct      1709
Pro Pro Ala Pro Ile Tyr Thr Pro Pro Pro Pro Ala Pro His Cys Pro
            510                 515                 520 ccc ccg ccc ccc agc gcc cct acc cct ccc atc ccg tcc cca cct tcc      1757
Pro Pro Pro Pro Ser Ala Pro Thr Pro Pro Ile Pro Ser Pro Pro Ser
            525                 530                 535 acc ctt ccc cct cct ccc cag gct cca cct ccc aac agg gca cct cct      1805
Thr Leu Pro Pro Pro Pro Gln Ala Pro Pro Pro Asn Arg Ala Pro Pro
        540                 545                 550 ccc tcc cgc cct cct cca agg cct tct gtc tagagcccaa agttcctgct        1855
Pro Ser Arg Pro Pro Pro Arg Pro Ser Val
555                 560 ctgggctctc tcagaaactt caggagatgt tagaacaagt ctttccagtt agagaagagg    1915
agtggtgata aagcccactg accttcacac attctaaaaa ttggttggca atgccagtat    1975
accaacaatc atgatcagct gaaagaaaca gatattttaa attgccagaa aacaaatgat    2035
gaggcaacta cagtcagatt tatagccagc catctatcac ctctagaagg ttccagagac    2095
agtgaaactg caagatgctc tcaacaggat tatgtctcat ggagaccagt aagaaaatca    2155
tttatctgaa ggtgaaatgc agagttggat aagaaataca ttgctgggtt tctaaaatgc    2215
tgccttcctg cctctactcc acctccatcc ctggactttg gacccttggc ctaggagcct    2275
aaggaccttc acccctgtgc caccccaag aaagaggaaa actttgccta caactttgga    2335
aatgctgggg tccctggtgt ggtaagaaac tcaacatcag acgggtatgc agaaggatgt    2395
tcttctggga tttgcaggta cataaaaaat gtatggcatc ttttccttgc aaattcttcc    2455
agtttccaag tgagaagggg agcaggtgtt tactgatgga aaaggtatgt tgctatgttg    2515
atgtgtaagt gaaatcagtt gtgtgcaata gacaggggcg tattcatggg agcatcagcc    2575
agtttctaaa acccacaggc catcagcagc tagaggtggc tggctttggc cagacatgga    2635
ccctaaatca acagacaatg gcattgtcga gagcaacct gttaatgaat catgttaaaa    2695
atcaaggttt ggcttcagtt taaatcactt gaggtatgaa gtttatcctg ttttccagag    2755
ataaacataa gttgatcttc ccaaaatacc atcattagga cctatcacac aatatcacta    2815
gttttttttg tttgtttgtt ttttgttttt tttcttggta aagccatgca ccacagactt    2875
ctgggcagag ctgagagaca atggtcctga cataataagg atctttgatt aacccccata    2935
aggcatgtgt gtgtatacaa atatacttct ctttggcttt tcgacataga acctcagctg    2995
ttaaccaagg ggaaatacat cagatctgca acacagaaat gctctgcctg aaatttccac    3055
catgcctagg actcacccca tttatccagg tctttctgga tctgtttaat caataagccc    3115
tataatcact tgctaaacac tgggcttcat cacccaggga taaaaacaga gatcattgtc    3175
```

```
ttggacctcc tgcatcagcc tattcaaaat tatctctctc tctagctttc cacaaatcct   3235
aaaattcctg tcccaagcca cccaaattct cagatctttt ctggaacaag gcagaatata   3295
aaataaatat acatttagtg gcttgggcta tggtctccaa agatccttca aaaatacatc   3355
aagccagctt cattcactca ctttacttag aacagagata taagggcctg ggatgcattt   3415 atttttatcaa taccaatttt tgtggccatg gcagacattg ctaatcaatc acagcactat   3475
ttcctattaa gcccactgat ttcttcacaa tccttctcaa attacaattc caaagagccg   3535
ccactcaaca gtcagatgaa cccaacagtc agatgagaga aatgaaccct acttgctatc   3595
tctatcttag aaagcaaaaa caaacaggag tttccaggga gaatgggaaa gccaggggc    3655 ataaaaggta cagtcagggg aaaatagatc taggcagagt gccttagtca gggaccacgg   3715
gcgctgaatc tgcagtgcca acaccaaact gacacatctc caggtgtacc tccaacccta   3775
gccttctccc acagctgcct acaacagagt ctcccagcct tctcagagag ctaaaaccag   3835
aaatttccag actcatgaaa gcaaccccccc agcctctccc caaccctgcc gcattgtcta   3895 attttttagaa cactaggctt cttctttcat gtagttcctc ataagcaggg gccagaatat   3955
ctcagccacc tgcagtgaca ttgctggacc cctgaaaacc attccatagg agaatgggtt   4015
ccccaggctc acagtgtaga gacattgagc ccatcacaac tgttttgact gctggcagtc   4075
taaaacagtc cacccacccc atggcactgc cgcgtgattc ccgcggccat tcagaagttc   4135
aagccgagat gctgacgttg ctgagcaacg agatggtgag catcagtgca aatgcaccat   4195
tcagcacatc agtcatatgc ccagtgcagt tacaagatgt tgtttcggca aagcatttg    4255 atggaatagg gaactgcaaa tgtatgatga ttttgaaaag gctcagcagg atttgttctt   4315
aaaccgactc agtgtgtcat ccccggttat ttagaattac agttaagaag gagaaacttc   4375
tataagactg tatgaacaag gtgatatctt catagtgggc tattacaggc aggaaaatgt   4435
tttaactggt ttacaaaatc catcaatact tgtgtcattc cctgtaaaag gcaggagaca   4495
tgtgattatg atcaggaaac tgcacaaaat tattgttttc agcccccgtg ttattgtcct   4555
tttgaactgt ttttttttta ttaaagccaa atttgtgttg tatatattcg tattccatgt   4615
gttagatgga agcatttcct atccagtgtg aataaaaaga acagttgtag taaattatta   4675
taaagccgat gatatttcat ggcaggttat tctaccaagc tgtgcttgtt ggttttttccc   4735 atgactgtat tgcttttata aatgtacaaa tagttactga aatgacgaga cccttgtttg   4795
cacagcatta ataagaacct tgataagaac catattctgt tgacagccag ctcacagttt   4855
cttgcctgaa gcttggtgca ccctccagtg agacacaaga tctctctttt accaaagttg   4915
agaacagagc tggtggatta attaatagtc ttcgatatct ggccatgggt aacctcattg   4975
taactatcat cagaatgggc agagatgatc ttgaagtgtc acatacacta aagtccaaac   5035
actatgtcag atgggggtaa aatccattaa agaacaggaa aaaataatta taagatgata   5095
agcaaatgtt tcagcccaat gtcaacccag ttaaaaaaaa aattaatgct gtgtaaaatg   5155
gttgaattag tttgcaaact atataaagac atatgcagta aaaagtctgt taatgcacat   5215
cctgtgggaa tggagtgttc taaccaattg ccttttcttg ttatctgagc tctcctatat   5275
tatcatactc agataaccaa attaaaagaa ttagaatatg attttttaata cacttaacat   5335 taaactcttc taactttctt ctttctgtga taattcagaa gatagttatg gatcttcaat   5395
gcctctgagt cattgttata aaaaatcagt tatcactata ccatgctata ggagactggg   5455 caaaaccctgt acaatgacaa ccctggaagt tgctttttt aaaaaaataa taaatttctt   5515
aaatcaaaaa aaaaaaaaaa aaaaa                                        5540
```

<210> SEQ ID NO 76
<211> LENGTH: 564
<212> TYPE: PRT
<213> ORGANISM: Homo sapiens

<400> SEQUENCE: 76

| Met | Ala | Thr | Ala | Glu | Arg | Arg | Ala | Leu | Gly | Ile | Gly | Phe | Gln | Trp | Leu |
|---|---|---|---|---|---|---|---|---|---|---|---|---|---|---|---|
| 1 | | | | 5 | | | | | 10 | | | | | 15 | |

Ser Leu Ala Thr Leu Val Leu Ile Cys Ala Gly Gln Gly Gly Arg Arg
        20                  25                  30

Glu Asp Gly Gly Pro Ala Cys Tyr Gly Gly Phe Asp Leu Tyr Phe Ile
            35                  40                  45

Leu Asp Lys Ser Gly Ser Val Leu His His Trp Asn Glu Ile Tyr Tyr
50                  55                  60

Phe Val Glu Gln Leu Ala His Lys Phe Ile Ser Pro Gln Leu Arg Met
65                  70                  75                  80

Ser Phe Ile Val Phe Ser Thr Arg Gly Thr Thr Leu Met Lys Leu Thr
                85                  90                  95

Glu Asp Arg Glu Gln Ile Arg Gln Gly Leu Glu Glu Leu Gln Lys Val
            100                 105                 110

Leu Pro Gly Gly Asp Thr Tyr Met His Glu Gly Phe Glu Arg Ala Ser
        115                 120                 125

Glu Gln Ile Tyr Tyr Glu Asn Arg Gln Gly Tyr Arg Thr Ala Ser Val
130                 135                 140

Ile Ile Ala Leu Thr Asp Gly Glu Leu His Glu Asp Leu Phe Phe Tyr
145                 150                 155                 160

Ser Glu Arg Glu Ala Asn Arg Ser Arg Asp Leu Gly Ala Ile Val Tyr
                165                 170                 175

Cys Val Gly Val Lys Asp Phe Asn Glu Thr Gln Leu Ala Arg Ile Ala
            180                 185                 190

Asp Ser Lys Asp His Val Phe Pro Val Asn Asp Gly Phe Gln Ala Leu
        195                 200                 205

Gln Gly Ile Ile His Ser Ile Leu Lys Lys Ser Cys Ile Glu Ile Leu
210                 215                 220

Ala Ala Glu Pro Ser Thr Ile Cys Ala Gly Glu Ser Phe Gln Val Val
225                 230                 235                 240

Val Arg Gly Asn Gly Phe Arg His Ala Arg Asn Val Asp Arg Val Leu
                245                 250                 255

Cys Ser Phe Lys Ile Asn Asp Ser Val Thr Leu Asn Glu Lys Pro Phe
            260                 265                 270

Ser Val Glu Asp Thr Tyr Leu Leu Cys Pro Ala Pro Ile Leu Lys Glu
        275                 280                 285

Val Gly Met Lys Ala Ala Leu Gln Val Ser Met Asn Asp Gly Leu Ser
290                 295                 300

Phe Ile Ser Ser Ser Val Ile Ile Thr Thr Thr His Cys Ser Asp Gly
305                 310                 315                 320

Ser Ile Leu Ala Ile Ala Leu Leu Ile Leu Phe Leu Leu Leu Ala Leu
                325                 330                 335

Ala Leu Leu Trp Trp Phe Trp Pro Leu Cys Cys Thr Val Ile Ile Lys
            340                 345                 350

Glu Val Pro Pro Pro Ala Glu Glu Ser Glu Glu Glu Asp Asp Asp
        355                 360                 365

Gly Leu Pro Lys Lys Lys Trp Pro Thr Val Asp Ala Ser Tyr Tyr Gly
370                 375                 380

-continued

```
Gly Arg Gly Val Gly Gly Ile Lys Arg Met Glu Val Arg Trp Gly Glu
385                 390                 395                 400

Lys Gly Ser Thr Glu Glu Gly Ala Lys Leu Glu Lys Ala Lys Asn Ala
                405                 410                 415

Arg Val Lys Met Pro Glu Gln Glu Tyr Glu Phe Pro Glu Pro Arg Asn
            420                 425                 430

Leu Asn Asn Asn Met Arg Arg Pro Ser Ser Pro Arg Lys Trp Tyr Ser
        435                 440                 445

Pro Ile Lys Gly Lys Leu Asp Ala Leu Trp Val Leu Leu Arg Lys Gly
    450                 455                 460

Tyr Asp Arg Val Ser Val Met Arg Pro Gln Pro Gly Asp Thr Gly Arg
465                 470                 475                 480

Cys Ile Asn Phe Thr Arg Val Lys Asn Asn Gln Pro Ala Lys Tyr Pro
            485                 490                 495

Leu Asn Asn Ala Tyr His Thr Ser Ser Pro Pro Pro Ala Pro Ile Tyr
        500                 505                 510

Thr Pro Pro Pro Ala Pro His Cys Pro Pro Pro Pro Pro Ser Ala
        515                 520                 525

Pro Thr Pro Pro Ile Pro Ser Pro Pro Ser Thr Leu Pro Pro Pro
    530                 535                 540

Gln Ala Pro Pro Asn Arg Ala Pro Pro Ser Arg Pro Pro Pro
545                 550                 555                 560

Arg Pro Ser Val
```